(12) United States Patent
Cazares et al.

(10) Patent No.: US 8,532,762 B2
(45) Date of Patent: Sep. 10, 2013

(54) DISCRIMINATING POLYMORPHIC AND MONOMORPHIC CARDIAC RHYTHMS USING TEMPLATE GENERATION

(75) Inventors: Shelley Cazares, Minneapolis, MN (US); Carlos Ricci, Apple Valley, MN (US); Dan Li, Shoreview, MN (US); Yayun Lin, St. Paul, MN (US); Yi Zhang, Blaine, MN (US); Jaeho Kim, Redmond, WA (US); Joseph Bocek, Seattle, WA (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 1486 days.

(21) Appl. No.: 11/312,279

(22) Filed: Dec. 20, 2005

(65) Prior Publication Data
US 2007/0142736 A1 Jun. 21, 2007

(51) Int. Cl.
*A61N 1/365* (2006.01)

(52) U.S. Cl.
USPC ...... 607/4; 607/9; 607/14; 600/508; 600/509; 600/510; 600/518

(58) Field of Classification Search
USPC .................. 607/4–5, 9, 14–15; 600/508–510; 600/515–523
See application file for complete search history.

(56) References Cited

U.S. PATENT DOCUMENTS

| | | |
|---|---|---|
| 4,023,564 A | 5/1977 | Valiquette |
| 4,336,810 A | 6/1982 | Anderson et al. |
| 4,428,378 A | 1/1984 | Anderson et al. |
| 4,774,950 A | 10/1988 | Cohen |
| 4,830,006 A | 5/1989 | Haluska et al. |
| 4,865,036 A | 9/1989 | Chirife |
| 5,002,052 A | 3/1991 | Haluska |
| 5,107,850 A | 4/1992 | Olive |
| 5,158,092 A | 10/1992 | Glace |
| 5,161,529 A | 11/1992 | Stotts et al. |

(Continued)

FOREIGN PATENT DOCUMENTS

| | | |
|---|---|---|
| EP | 0467695 | 1/1992 |
| EP | 0547733 | 6/1993 |

(Continued)

OTHER PUBLICATIONS

Dubin, Rapid Interpretation of EKG's, 2000, Cover Publishing Company, 6th Edition, p. 334-345.

(Continued)

*Primary Examiner* — Niketa Patel
*Assistant Examiner* — Hiba El-Kaissi
(74) *Attorney, Agent, or Firm* — Brooks, Cameron & Huebsch, PLLC

(57) ABSTRACT

Cardiac arrhythmias are classified based on the morphology of the arrhythmia episode beats. Templates are formed using morphological features of the cardiac beats of the episode. The arrhythmia episode is classified as a monomorphic tachyarrhythmia or polymorphic tachyarrhythmia based on the one or more templates. The arrhythmia episode may be classified based on a number templates formed from the arrhythmia episode. The templates are formed by determining a measure of similarity between morphological features of a cardiac beat to a template. The similarities can be determined based on a pairing rule that determines which beat morphologies are compared. Selection of therapy for treating the arrhythmia episode may depend on the historical success of a therapy at mitigating previous arrhythmias of the same type as the arrhythmia episode.

22 Claims, 13 Drawing Sheets

(56) References Cited

U.S. PATENT DOCUMENTS

| | | |
|---|---|---|
| 5,176,137 A | 1/1993 | Erickson et al. |
| 5,181,511 A | 1/1993 | Nickolls et al. |
| 5,193,550 A | 3/1993 | Duffin |
| 5,209,229 A | 5/1993 | Gilli |
| 5,217,021 A | 6/1993 | Steinhaus et al. |
| 5,222,493 A | 6/1993 | Sholder |
| 5,224,475 A | 7/1993 | Berg et al. |
| 5,251,621 A | 10/1993 | Collins |
| 5,251,624 A | 10/1993 | Bocek et al. |
| 5,257,621 A | 11/1993 | Bardy et al. |
| 5,312,441 A | 5/1994 | Mader et al. |
| 5,312,445 A | 5/1994 | Nappholz et al. |
| 5,324,310 A | 6/1994 | Greeninger et al. |
| 5,330,505 A | 7/1994 | Cohen |
| 5,330,508 A | 7/1994 | Gunderson |
| 5,342,402 A | 8/1994 | Olson et al. |
| 5,350,410 A | 9/1994 | Kleks et al. |
| 5,379,776 A | 1/1995 | Murphy et al. |
| 5,425,749 A | 6/1995 | Adams |
| 5,447,519 A | 9/1995 | Peterson |
| 5,458,620 A | 10/1995 | Adams |
| 5,472,453 A | 12/1995 | Alt |
| 5,513,644 A | 5/1996 | McClure et al. |
| 5,548,619 A | 8/1996 | Horiike et al. |
| 5,554,177 A | 9/1996 | Kieval |
| 5,587,970 A | 12/1996 | Greenwood |
| 5,662,688 A | 9/1997 | Haefner et al. |
| 5,683,424 A | 11/1997 | Brown et al. |
| 5,683,431 A | 11/1997 | Wang |
| 5,685,315 A | 11/1997 | McClure et al. |
| 5,725,559 A | 3/1998 | Alt et al. |
| 5,755,737 A | 5/1998 | Prieve et al. |
| 5,779,645 A | 7/1998 | Olson et al. |
| 5,782,888 A | 7/1998 | Sun et al. |
| 5,817,027 A | 10/1998 | Arand et al. |
| 5,836,971 A | 11/1998 | Starkweather |
| 5,855,593 A | 1/1999 | Olson et al. |
| 5,857,977 A | 1/1999 | Caswell et al. |
| 5,871,512 A | 2/1999 | Hemming et al. |
| 5,893,882 A | 4/1999 | Peterson et al. |
| 5,978,707 A | 11/1999 | Krig et al. |
| 5,999,851 A | 12/1999 | White |
| 6,064,906 A * | 5/2000 | Langberg et al. ............. 600/518 |
| 6,076,014 A | 6/2000 | Alt |
| 6,101,414 A | 8/2000 | Kroll |
| 6,128,529 A | 10/2000 | Esler |
| 6,137,308 A | 10/2000 | Nayak |
| 6,151,524 A | 11/2000 | Krig et al. |
| 6,167,308 A | 12/2000 | Degroot |
| 6,178,350 B1 | 1/2001 | Olson et al. |
| 6,185,459 B1 | 2/2001 | Mehra et al. |
| 6,192,275 B1 | 2/2001 | Zhu et al. |
| 6,212,428 B1 | 4/2001 | Hsu et al. |
| 6,221,011 B1 | 4/2001 | Bardy |
| 6,223,078 B1 | 4/2001 | Marcovecchio |
| 6,230,055 B1 | 5/2001 | Sun |
| 6,253,102 B1 | 6/2001 | Hsu et al. |
| 6,266,554 B1 | 7/2001 | Hsu |
| 6,270,457 B1 | 8/2001 | Bardy |
| 6,275,732 B1 | 8/2001 | Hsu et al. |
| 6,277,072 B1 | 8/2001 | Bardy |
| 6,280,380 B1 | 8/2001 | Bardy |
| 6,289,248 B1 | 9/2001 | Conley et al. |
| 6,308,095 B1 | 10/2001 | Hsu et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,393,316 B1 | 5/2002 | Gillberg et al. |
| 6,398,728 B1 | 6/2002 | Bardy |
| 6,400,986 B1 | 6/2002 | Sun |
| 6,434,417 B1 | 8/2002 | Lovett |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,477,422 B1 | 11/2002 | Splett |
| 6,480,734 B1 | 11/2002 | Zhang et al. |
| 6,487,443 B2 | 11/2002 | Olson et al. |
| 6,490,478 B1 | 12/2002 | Zhang et al. |
| 6,564,106 B2 | 5/2003 | Guck et al. |
| 6,611,713 B2 | 8/2003 | Schauerte |
| 6,631,290 B1 | 10/2003 | Guck et al. |
| 6,636,764 B1 | 10/2003 | Fain et al. |
| 6,654,639 B1 | 11/2003 | Lu |
| 6,684,100 B1 | 1/2004 | Sweeney |
| 6,708,058 B2 | 3/2004 | Kim et al. |
| 6,731,982 B1 | 5/2004 | Kroll et al. |
| 6,766,194 B1 | 7/2004 | Kroll |
| 6,801,806 B2 | 10/2004 | Sun et al. |
| 6,882,883 B2 | 4/2005 | Condie et al. |
| 6,885,890 B2 | 4/2005 | Spinelli et al. |
| 6,889,079 B2 | 5/2005 | Bocek et al. |
| 6,909,916 B2 | 6/2005 | Spinelli |
| 6,922,585 B2 | 7/2005 | Zhou |
| 7,031,764 B2 | 4/2006 | Schwartz et al. |
| 7,031,771 B2 | 4/2006 | Brown et al. |
| 7,076,289 B2 | 7/2006 | Sakar et al. |
| 7,103,405 B2 | 9/2006 | Sakar et al. |
| 7,107,098 B2 | 9/2006 | Sharma et al. |
| 7,129,935 B2 | 10/2006 | Mackey |
| 7,130,677 B2 | 10/2006 | Brown et al. |
| 7,130,678 B2 | 10/2006 | Ritscher et al. |
| 7,184,815 B2 | 2/2007 | Kim et al. |
| 7,228,173 B2 | 6/2007 | Cazares |
| 7,277,747 B2 | 10/2007 | Cazares et al. |
| 7,330,757 B2 | 2/2008 | Ostroff et al. |
| 7,477,932 B2 | 1/2009 | Lee |
| 7,558,623 B2 | 7/2009 | Fischell et al. |
| 7,706,866 B2 | 4/2010 | Zhang et al. |
| 7,725,184 B2 | 5/2010 | Cazares |
| 7,729,762 B2 | 6/2010 | Sun |
| 2002/0183637 A1 | 12/2002 | Kim et al. |
| 2003/0144700 A1 | 7/2003 | Brown et al. |
| 2003/0191403 A1 | 10/2003 | Zhou et al. |
| 2004/0093035 A1 | 5/2004 | Schwartz et al. |
| 2004/0111119 A1 | 6/2004 | Sakar |
| 2004/0111120 A1 | 6/2004 | Sakar |
| 2004/0111121 A1 * | 6/2004 | Brown et al. ............. 607/5 |
| 2004/0167579 A1 | 8/2004 | Sharma et al. |
| 2004/0171959 A1 | 9/2004 | Staler et al. |
| 2004/0176694 A1 | 9/2004 | Kim et al. |
| 2004/0243014 A1 * | 12/2004 | Lee et al. ............. 600/510 |
| 2004/0254613 A1 | 12/2004 | Ostroff et al. |
| 2005/0137485 A1 * | 6/2005 | Cao et al. ............. 600/510 |
| 2005/0137641 A1 | 6/2005 | Naughton |
| 2005/0192506 A1 | 9/2005 | Kim et al. |
| 2006/0074331 A1 | 4/2006 | Kim et al. |
| 2006/0111747 A1 | 5/2006 | Cazares et al. |
| 2006/0217621 A1 | 9/2006 | Kim et al. |
| 2006/0253044 A1 | 11/2006 | Zhang et al. |
| 2006/0281998 A1 | 12/2006 | Li et al. |
| 2007/0049974 A1 * | 3/2007 | Li et al. ............. 607/4 |

FOREIGN PATENT DOCUMENTS

| | | |
|---|---|---|
| EP | 0253505 | 2/1994 |
| EP | 0360412 | 3/1995 |
| EP | 0709112 | 5/1996 |
| EP | 0801960 | 10/1997 |
| EP | 1267993 | 3/2001 |
| WO | WO9840122 | 9/1998 |
| WO | WO 02/ 24276 | 3/2002 |
| WO | WO 03092810 | 11/2003 |
| WO | 03047690 | 12/2003 |
| WO | WO2006039694 | 4/2006 |

OTHER PUBLICATIONS

Mercando et al., Measurement of Differences in Timing and Sequence Between Two Ventricular Electrodes as a Means of Tachycardia Differentiation, PACE, Part II, vol. 9, Nov.-Dec. 1986, 1069-1078. (abstract only).

Office Action from U.S. Appl. No. 11/209,976 dated Nov. 20, 2009, 11 pages.

Office Action from U.S. Appl. No. 11/089,185 dated Nov. 3, 2009, 7 pages.
Office Action from U.S. Appl. No. 11/089,185 dated May 15, 2009, 11 pages.
Office Action from U.S. Appl. No. 11/089,185 dated Dec. 8, 2008, 8 pages.
Office Action from U.S. Appl. No. 11/089,185 dated Mar. 28, 2008, 14 pages.
File History for U.S. Appl. No. 10/955,831.
File History for U.S. Appl. No. 10/995,704.
File History for U.S. Appl. No. 11/209,976.
U.S. Appl. No. 11/151,102.
U.S. Appl. No. 11/038,996.
U.S. Appl. No. 10/995,655, filed Nov. 23, 2004, Cazares.
U.S. Appl. No. 10/995,704, filed Nov. 23, 2004, Cazares.
U.S. Appl. No. 10/995,831, filed Sep. 30, 2004, Kim.
U.S. Appl. No. 11/209,976, filed Aug. 23, 2005, Li.
File History for European Application No. 11075091.6.
File History for U.S. Appl. No. 12/708,106.
File History for U.S. Appl. No. 12/771,691.
Office Action dated Jan. 4, 2012 for Japanese Application No. 2008-528096, 6 pages.
Office Action dated Mar. 27, 2012 for Japanese Application No. 2008-547299, 3 pages.
File History for EP Application No. 05800765.9.
Office Action Response dated Jun. 8, 2012 for Japanese Application No. 2008-528096, 7 pages.
Office Action dated Mar. 28, 2008 from U.S. Appl. No. 11/089,185, 8 pages.
Office Action Response dated Jun. 30, 2008 from U.S. Appl. No. 11/089,185, 13 pages.
Office Action dated Dec. 8, 2008 from U.S. Appl. No. 11/089,185, 6 pages.
Office Action Response dated Apr. 8, 2009 from U.S. Appl. No. 11/089,185, 9 pages.
Office Action dated May 15, 2009 from U.S. Appl. No. 11/089,185, 6 pages.
Office Action dated Jul. 24, 2009 from U.S. Appl. No. 11/089,185, 2 pages.
Office Action Response dated Aug. 4, 2009 from U.S. Appl. No. 11/089,185, 10 pages.
Office Action dated Nov. 3, 2009 U.S. Appl. No. 11/089,185, 6 pages.
Office Action dated Jan. 13, 2010 from U.S. Appl. No. 11/089,185, 3 pages.
Office Action Response dated Jan. 27, 2010 from U.S. Appl. No. 11/089,185, 10 pages.
Office Action dated Mar. 24, 2010 from U.S. Appl. No. 11/089,185, 6 pages.
Office Action Response dated May 20, 2010 from U.S. Appl. No. 11/089,185, 11 pages.
Notice of Allowance dated Jun. 11, 2010 from U.S. Appl. No. 11/089,185, 4 pages.
Notice of Allowance dated Jul. 22, 2010 from U.S. Appl. No. 11/089,185, 4 pages.
Office Action dated Jul. 18, 2006 from U.S. Appl. No. 10/995,655, 9 pages.
Office Action Response dated Oct. 23, 2006 from U.S. Appl. No. 10/995,655, 14 pages.
Notice of Allowance dated Jan. 9, 2007 from U.S. Appl. No. 10/995,655, 9 pages.
Office Action dated Sep. 11, 2009 from U.S. Appl. No. 11/807,696, 10 pages.
Office Action dated Nov. 23, 2009 from U.S. Appl. No. 11/807,696, 3 pages.
Office Action Response dated Dec. 11, 2009 from U.S. Appl. No. 11/807,696, 9 pages.
Notice of Allowance dated Jan. 15, 2010 from U.S. Appl. No. 11/807,696, 7 pages.
Office Action dated Feb. 13, 2007 from U.S. Appl. No. 10/995,704, 9 pages.
Office Action Response dated May 18, 2007 from U.S. Appl. No. 10/995,704, 17 pages.
Office Action dated Aug. 23, 2007 from U.S. Appl. No. 10/995,704, 8 pages.
Office Action Response dated Oct. 25, 2007 from U.S. Appl. No. 10/995,704, 12 pages.
Office Action dated Nov. 20, 2007 from U.S. Appl. No. 10/995,704, 3 pages.
Pre-Appeal Brief dated Jan. 28, 2008 from U.S. Appl. No. 10/995,704, 6 pages.
Appeal Brief date Apr. 25, 2008 from U.S. Appl. No. 10/995,704, 30 pages.
Examiner Answer dated Jul. 25, 2008 from U.S. Appl. No. 10/995,704, 8 pages.
Reply Brief dated Sep. 25, 2008 from U.S. Appl. No. 10/995,704, 10 pages.
Office Action dated Apr. 22, 2008 from U.S. Appl. No. 11/209,976, 9 pages.
Office Action Response dated May 27, 2008 from U.S. Appl. No. 11/209,976, 7 pages.
Office Action dated Aug. 29, 2008 from U.S. Appl. No. 11/209,976, 10 pages.
Office Action Response dated Dec. 18, 2008 from U.S. Appl. No. 11/209,976, 11 pages.
Office Action dated Apr. 16, 2009 from U.S. Appl. No. 11/209,976, 9 pages.
Office Action dated Jul. 10, 2009 from U.S. Appl. No. 11/209,976, 10 pages.
Office Action Response dated Sep. 3, 2009 from U.S. Appl. No. 11/209,976, 7 pages.
Office Action dated Nov. 20, 2009 from U.S. Appl. No. 11/209,976, 10 pages.
Office Action Response dated Feb. 17, 2010 from U.S. Appl. No. 11/209,976, 10 pages.
Office Action dated Apr. 22, 2010 from U.S. Appl. No. 11/209,976, 12 pages.
Office Action Response dated Jun. 22, 2010 from U.S. Appl. No. 11/209,976, 11 pages.
Office Action dated Jul. 13, 2010 from U.S. Appl. No. 11/209,976, 4 pages.
Office Action dated May 1, 2008 from U.S. Appl. No. 11/267,071, 7 pages.
Office Action dated Sep. 24, 2008 from U.S. Appl. No. 11/267,071, 2 pages.
Office Action Response dated Oct. 23, 2008 from U.S. Appl. No. 11/267,071, 13 pages.
Office Action dated Jan. 16, 2009 from U.S. Appl. No. 11/267,071, 8 pages.
Office Action Response dated Apr. 15, 2009 from U.S. Appl. No. 11/267,071, 9 pages.
Office Action dated Jun. 12, 2009 from U.S. Appl. No. 11/267,071, 5 pages.
Office Action Response dated Sep. 10, 2009 from U.S. Appl. No. 11/267,071, 10 pages.
Notice of Allowance dated Dec. 17, 2009 from U.S. Appl. No. 11/267,071, 4 pages.
Office Action dated Jun. 16, 2009 from European Application No. 05800765.9, 3 pages.
Office Action Response dated Dec. 15, 2009 from European Application No. 05800765.9, 39 pages.
International Preliminary Report on Patentability dated Apr. 12, 2007 from PCT Application No. PCT/US2005/035641, 9 pages.
International Preliminary Report on Patentability dated Jul. 3, 2008 from PCT Application No. PCT/US2006/047215, 8 pages.
International Preliminary Report on Patentability dated Mar. 6, 2008 from PCT Application No. PCT/US2006/032872, 6 pages.
International Search Report and Written Opinion dated Jun. 12, 2006 from PCT Application No. PCT/US2005/035641, 20 pages.
International Search Report and Written Opinion dated Jun. 19, 2007 from PCT Application No. PCT/US2006/047215, 13 pages.
International Search Report and Written Opinion dated Feb. 12, 2007 from PCT Application No. PCT/US2006/032872, 8 pages.
Invitation to Pay Additional Fees dated Jan. 3, 2006 from PCT Application No. PCT/US2005/035641, 8 pages.

Lake et al., Sample entropy analysis of neonatal heart rate variability, An. J. Physiol Reguul Integr omp Physiol., vol. 283, 2002.

Office Action dated Jul. 12, 2011 for JP Application No. 2007-534885, 2 pages.

U.S. Appl. No. 11/312,280, filed Dec. 20, 2005, Cazares et al.

U.S. Appl. No. 11/089,185, filed Mar. 24, 2005, Kim et al.

"VITALITY 2 Implantable Cardioverter Defibrillator System Guide", Guidant Corporation, 2004, Cover pages and pp. 3-15 to 3-19.

Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, Nov. 2002, pp. 1092-1097.

M. S. Wathen, M.D. et al. Shock Reduction Using Antitachycardia Pacing for Spontaneous Rapid Ventricular Tachycardia in Patients with Coronary Artery Disease. *Circulation 2001*, vol. 104:796-801. © 2001 American Heart Association, Inc.

Martha Kerr. Shock Rate Cut 70% with ICDs Programmed to First Deliver Antitachycardia Pacing: Results of the PainFREE Rx II Trial. *NewsRhythms*. MedScape CRM News 2003. www.medscape.com.

Lake et al., *Am. J. Physiol. Regul. Integr. Comp. Physiol.*, 283: R789-97 (2002).

Richman et al., *Am. J. Physiol. Heart Circ. Physiol.*, 278: H2039-49 (2000).

Office Action dated Sep. 10, 2012 for U.S. Appl. No. 13/048,582, 16 pages.

* cited by examiner

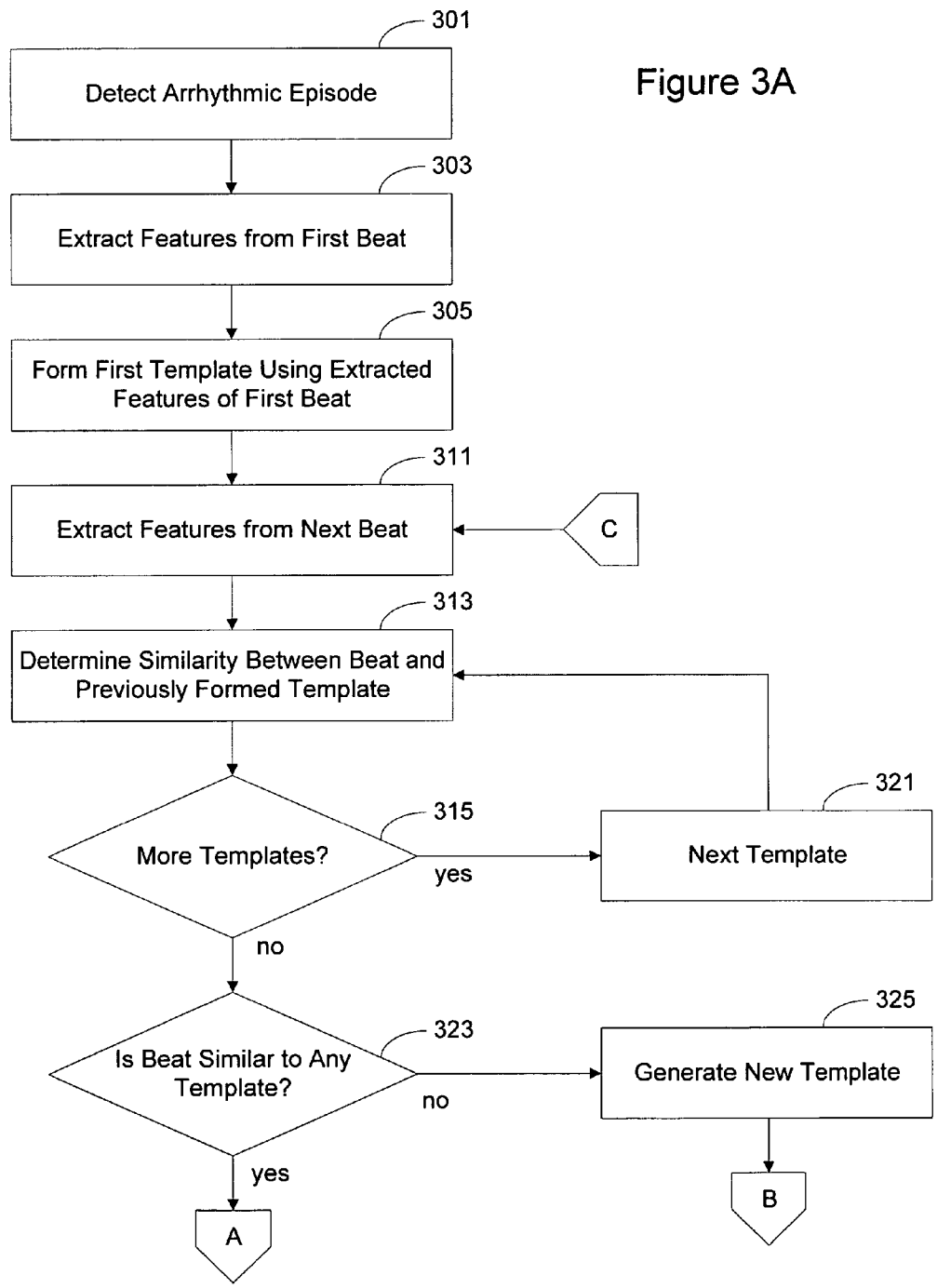

DISCRIMINATING POLYMORPHIC AND MONOMORPHIC CARDIAC RHYTHMS USING TEMPLATE GENERATION

FIELD OF THE INVENTION

The present invention relates generally to implantable medical devices, and more particularly, to classifying cardiac rhythms and providing arrhythmia therapy.

BACKGROUND OF THE INVENTION

Rhythmic contractions of a healthy heart are normally initiated by the sinoatrial (SA) node, specialized cells located in the upper right atrium. The SA node is the normal pacemaker of the heart. When functioning normally, the heart produces rhythmic contractions and is capable of pumping blood throughout the body. However, due to disease or injury, the heart rhythm may become irregular resulting in diminished blood circulation. Arrhythmia is a general term used to describe heart rhythm irregularities arising from a variety of physical conditions and disease processes.

A cardiac tachyarrhythmia that originates in a non-ventricular region of the heart is denoted a supra-ventricular tachyarrhythmia (SVT). Atrial fibrillation and atrial flutter are examples of SVT. Both conditions are characterized by rapid contractions of the atria resulting in hemodynamically inefficient pumping action.

Cardiac arrhythmias originating in a ventricular region of the heart are denoted ventricular tachyarrhythmias (VT). Some types of ventricular tachyarrhythmia are characterized by rapid ventricular contractions that are fairly regular and coordinated. Such rhythms can degenerate into ventricular fibrillation (VF). Ventricular fibrillation produces extremely rapid, non-coordinated contractions of the ventricles and is fatal unless the heart is returned to sinus rhythm within a few minutes.

Implantable cardiac rhythm management (CRM) devices, including pacemakers and implantable cardioverter/defibrillators (ICDs), have been used to deliver effective treatment to patients with serious cardiac arrhythmias. Leads extending into the patient's heart are connected to electrodes electrically coupled to the myocardium for sensing the heart's electrical signals and for delivering stimulation pulses to the heart in accordance with various therapies for treating the arrhythmias.

A number of CRM devices having various modes for sensing and delivering electrical stimulation to one or more heart chambers can treat cardiac arrhythmias using a variety of tiered therapies. These tiered therapies range from the delivery of low energy pacing pulses timed to assist the heart in maintaining pumping efficiency to high energy shocks to terminate fibrillation. To effectively deliver these treatments the CRM device must first identify the type of arrhythmia that is occurring.

For the reasons stated above, and for other reasons stated below which will become apparent to those skilled in the art upon reading the present specification, there is a need in the art for methods and systems that accurately identify cardiac arrhythmias. There exists a further need to deliver effective cardiac therapy. The present invention fulfills these and other needs.

SUMMARY OF THE INVENTION

Various embodiments of present invention are directed to methods and systems for classifying types of cardiac arrhythmia and for selecting therapies to treat the arrhythmias. One embodiment involves a method of arrhythmia discrimination for implementation by a cardiac rhythm management device. The method includes detecting cardiac beats associated with an arrhythmia episode. One or more templates are formed using morphological features of the cardiac beats of the arrhythmia episode. The arrhythmia episode is determined to be monomorphic tachyarrhythmia or polymorphic tachyarrhythmia based on the templates. For example, the arrhythmia episode may be determined to be monomorphic tachyarrhythmia or polymorphic tachyarrhythmia based on the number of templates formed from the arrhythmia episode beats.

A template may be formed based on a measure of similarity between morphological features of a cardiac beat to a template formed by one or more previous beats. An additional template may be formed from the beat or a previously formed template may be modified by the beat based on the measure of similarity. The arrhythmia episode may be determined to be monomorphic tachyarrhythmia or polymorphic tachyarrhythmia based on the similarity of the one or more templates formed from the arrhythmia episode.

A pairing rule may be used to determine the similarity of the templates. In one implementation, the pairing rule is used to determine the similarity of the templates based on comparison of pairs of adjacent cardiac beats. In another implementation, the pairing rule involves comparing a most recent template to each prior template. In yet another implementation, the pairing rule involves comparing all possible template combinations. From the template comparison, a morphology regularity of the one or more templates is measured.

In some implementations, forming the templates and/or classifying the arrhythmia episode is performed during the arrhythmia episode. In other implementations, forming the templates and/or classifying the arrhythmia episode is performed after the arrhythmia episode has terminated.

According to one aspect of the invention, a particular template of the templates may be stored as representative of the arrhythmia episode. Subsequent monomorphic arrhythmia episodes may be classified according to monomorphic arrhythmia type using the stored template.

The classification of the arrhythmia episode performed using the processes of the present invention may be used to confirm a separate classification by another process.

Arrhythmia episodes determined to be monomorphic arrhythmia episodes may be further classified according to monomorphic arrhythmia type. The method may further include selecting a therapy based on the classification of the arrhythmia episode according to monomorphic arrhythmia type. For example, the therapy may be selected based on a history of success of the therapy at mitigating previous arrhythmias of the same type as the arrhythmia episode.

Another embodiment of the invention is directed to an implantable medical device. The medical device includes sensor circuitry comprising electrodes for electrically coupling to a heart. The sensor circuitry is configured to detect cardiac beats associated with a cardiac arrhythmia episode. A template generator is coupled to the sensor circuitry and is configured to form one or more templates using the detected cardiac beats. An arrhythmia processor is configured to determine if the arrhythmia episode is monomorphic tachyarrhythmia or polymorphic tachyarrhythmia based on the one or more templates.

The one or more templates are formed by the template generator using similar cardiac beats. In one implementation, the arrhythmia processor is configured to determine if the arrhythmia episode is monomorphic tachyarrhythmia or polymorphic tachyarrhythmia based on the number of templates formed. In another implementation, the arrhythmia processor is configured to determine if the arrhythmia episode is monomorphic tachyarrhythmia or polymorphic tachyarrhythmia based on a similarity of the one or more templates. The similarity of the one or more templates may be determined based on a pairing rule.

The medical device may also include a memory for storing particular templates which are representative of the arrhythmia episode. The arrhythmia processor is configured to classify subsequently detected monomorphic tachyarrhythmia episodes according to monomorphic arrhythmia type using the one or more particular templates.

The medical device may also include a control system configured to select an electrical stimulation therapy based on at least one of the determination that the arrhythmia episode is monomorphic tachyarrhythmia or polymorphic tachyarrhythmia and the classification of the arrhythmia episode according to monomorphic arrhythmia types. Therapy circuitry is coupled to the control system and is configured to deliver the electrical stimulation therapy to a heart. In some implementations, the therapy is selected by the control system based on a history of success at mitigating the type of arrhythmia associated with the arrhythmia episode.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 3A-3C provide a flowchart illustrating the polymorphic tachyarrhythmia/monomorphic tachyarrhythmia discrimination and tachyarrhythmia template generation processes in accordance with embodiments of the invention;

Figure 1A:
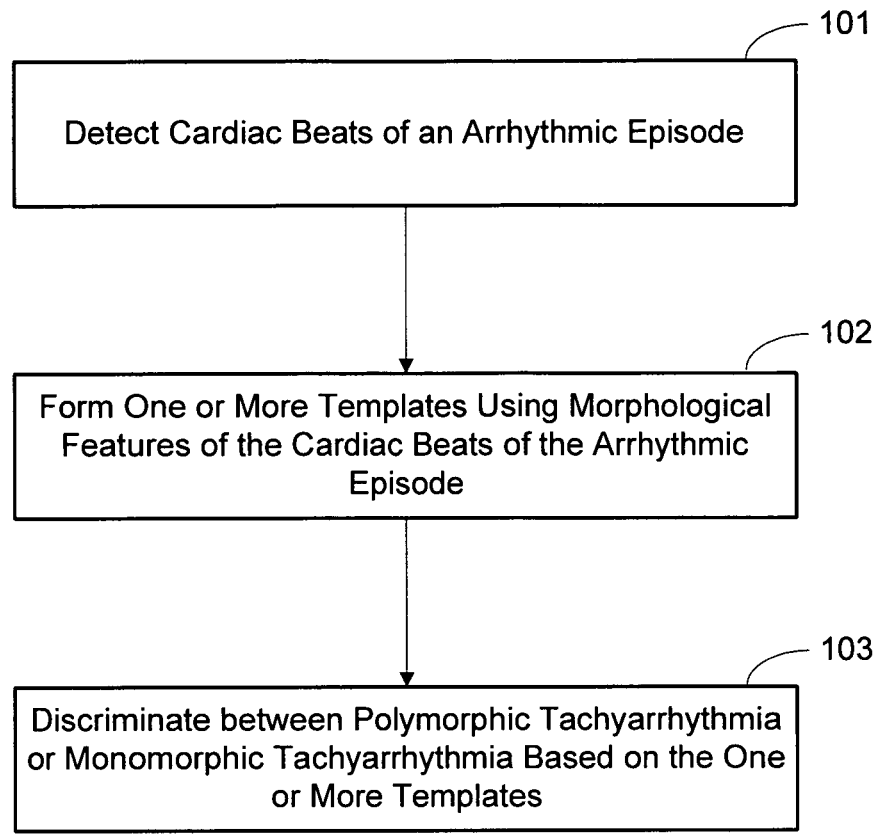
FIG. 1A is a flowchart of a method of discriminating between monomorphic and polymorphic ventricular tachyarrhythmia using template generation in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown, by way of illustration, various embodiments in which the invention may be practiced. It is to be understood that other embodiments may be utilized, and structural and functional changes may be made, without departing from the scope of the present invention.

Ventricular tachyarrhythmias are fast heart rhythms that arise within one or more ventricles. Atrial tachyarrhythmias, e.g., atrial flutter or atrial fibrillation, are fast heart rhythms that arise within one or more atria. Cardiac electrical signals representative of ventricular or atrial tachyarrhythmia beats may are sensed using cardiac electrodes electrically coupled to the heart and associated sensing circuitry. The morphologies of cardiac signals produced by beats of tachyarrhythmia episodes may involve a number of different morphologies. Some types of tachyarrhythmia produce cardiac beats having signal waveforms that exhibit a fairly regular rhythm and a similar shape or morphology. These tachyarrhythmia episodes are denoted monomorphic tachyarrhythmia (MT). A patient may exhibit different types of MTs, each MT recognizable by a characteristic morphology. Various MT types may be identified using cardiac beat templates that are representative of the characteristic morphologies associated with the MT types.

The cardiac beat waveforms of other tachyarrhythmia episodes may have a disorganized, inconsistent morphology from beat to beat. These tachyarrhythmia episodes are denoted polymorphic tachyarrhythmia (PT). Ventricular fibrillation is an example of a polymorphic ventricular tachyarrhythmia. Polymorphic tachyarrhythmias can not be represented using cardiac beat morphology templates because the morphology of PT is inconsistent from beat to beat.

Episodes of tachyarrhythmia may last only a few beats and may produce minimal symptoms. If the cardiac rate is relatively low, the tachyarrhythmia may be tolerated even if sustained for a number of minutes. Tachyarrhythmia may be treated using a variety of therapies. For example, in some cases, ventricular tachyarrhythmia (VT) may be effectively treated by pacing at relatively high energy output when compared to bradycardia pacing. Pacing to mitigate VT may involve one or more pacing bursts and is typically denoted anti-tachycardia pacing (ATP). Other types of VT may require a more aggressive therapy, including high energy cardioversion and/or defibrillation shocks. Still other types of VT may terminate spontaneously without therapy.

The most dangerous form of polymorphic ventricular tachyarrhythmia is ventricular fibrillation, which involves very rapid, small-scale, and uncoordinated contractions. The rapid contractions cause a precipitous drop in blood pressure and low cardiac output. Ventricular fibrillation involving heart rates in excess of about 220 beats per minute rarely terminate spontaneously and may be fatal without rapid therapeutic intervention. Typically therapy for ventricular fibrillation involves a series of high energy defibrillation shocks.

Various embodiments of the invention are directed to an automated process for comparing the morphologies of cardiac beats of a tachyarrhythmic episode to discriminate between MT and PT and to return a template representing the overall morphology of the cardiac beats of the tachyarrhythmic episode. The PT/MT discrimination processes described herein may be used for PT/MT discrimination for supraventricular tachyarrhythmia (SVTs). The PT/MT discrimination processes described herein may additionally or alternatively be used for PT/MT discrimination for ventricular tachyarrhythmias (VTs). A morphology template formed for an MT episode using beats of the MT episode may be returned for use in classifying subsequent MT episodes as corresponding to the particular type of MT characterized by the template. An appropriate therapy may be selected based on whether the tachyarrhythmia episode is PT or MT, and, if the arrhythmia episode is MT, the type of MT.

FIG. 1A illustrates a process for determining if a tachyarrhythmia episode is MT or PT in accordance with embodiments of the invention. Cardiac beats of an arrhythmia episode are detected 101. One or more templates are formed 102 using morphological features of the cardiac beat waveforms. The arrhythmia episode is discriminated 103 as a PT episode or a MT episode based on similarity of the templates formed.

Figure 1B:
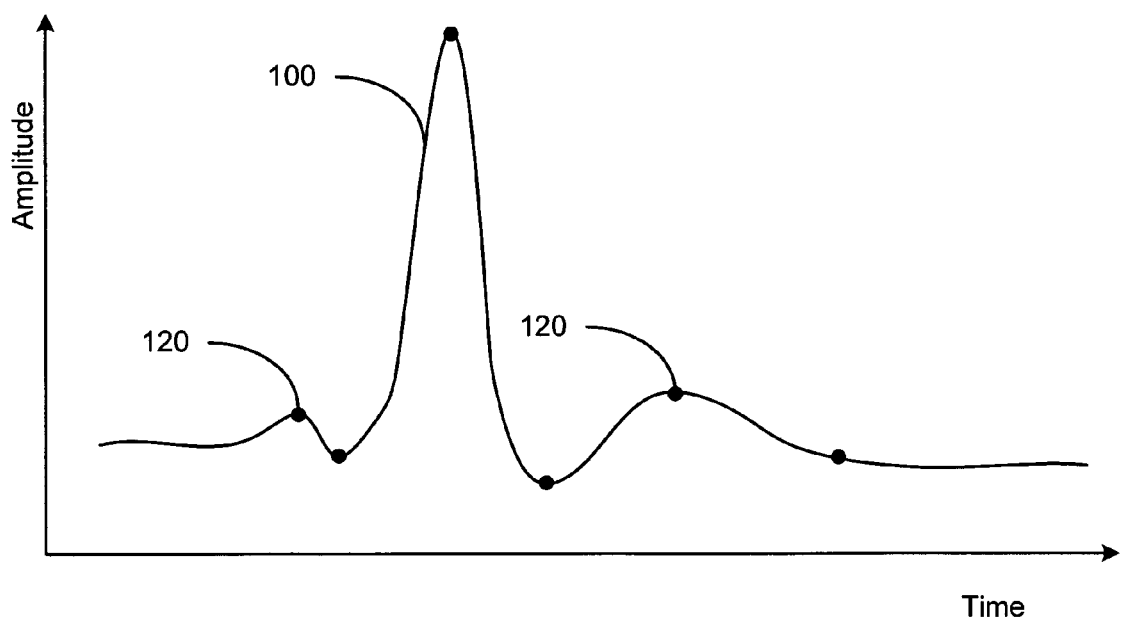
FIG. 1B illustrates the morphology of a cardiac beat signal waveform with identification of signal features that may be extracted for template creation and/or for comparison with templates created using previous beats of the arrhythmia episode in accordance with embodiments of the invention.

In one example, the templates are formed using samples or waveform features extracted from the cardiac beat waveforms. The samples or waveform features may be used to form a template that characterizes a particular type of MT. FIG. 1B illustrates the morphology of a cardiac beat signal waveform with identification of signal features that may be extracted for template creation and/or for comparison with templates formed using previous beats of the arrhythmia episode in accordance with embodiments of the invention.

As illustrated in FIG. 1B, a cardiac waveform 100 representing a particular beat morphology is sensed and one or more cardiac waveform features 120 are detected. A waveform feature 120 may include a particular point of a cardiac signal waveform 100. The waveform features 120 may be identified based on various morphological aspects of the cardiac waveform, such as critical points, local extrema, inflection points, rise or fall times, slopes, areas above and/or below the waveform, and frequency and/or wavelet coefficients, or by other aspects, as is known in the art.

Figure 2:
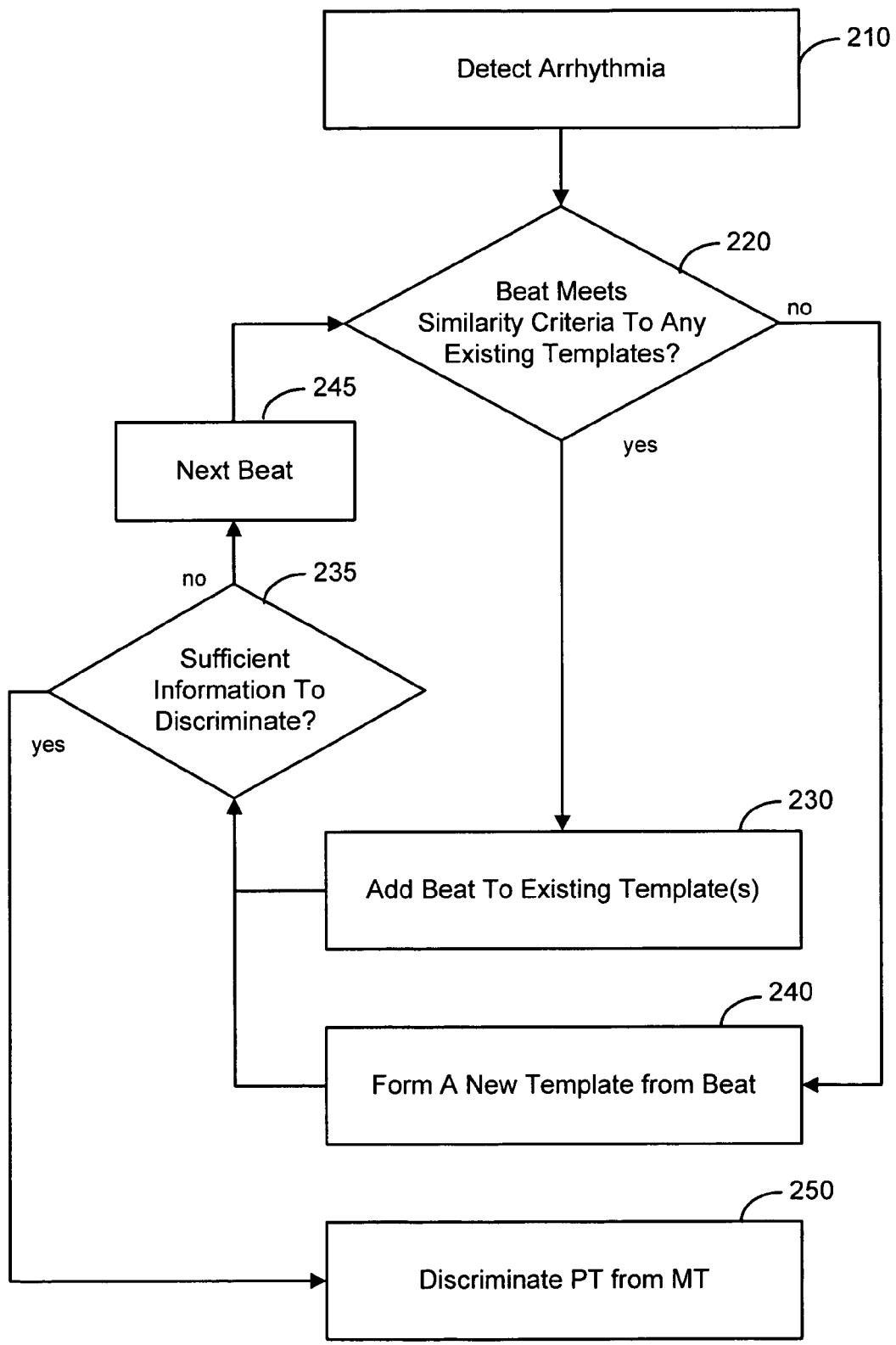
FIG. 2 is a flowchart illustrating a method for discriminating between polymorphic ventricular tachyarrhythmia and monomorphic ventricular tachyarrhythmia using template generation in accordance with embodiments of the invention.

FIG. 2 is a flowchart illustrating a method for discriminating between polymorphic ventricular tachyarrhythmia (PVT) and monomorphic ventricular tachyarrhythmia (MVT) using template generation in accordance with embodiments of the invention. An arrhythmia episode is detected 210, for example, based on the heart rate exceeding a predetermined threshold. For example, ventricular tachyarrhythmia may initially be detected based on ventricular rate by evaluating the patient's V-V intervals. If the system detects a ventricular rate above a threshold, then the system flags the episode as a tachyarrhythmia episode. The tachyarrhythmia rate may be categorized as a relatively fast, medium, or slow tachyarrhythmia based on a number or percentage of intervals, e.g., V-V intervals, that fall within specified ranges for relatively fast, medium, or slow tachyarrhythmia.

After the tachyarrhythmia is initially detected 210 based on rate, a morphological analysis process is implemented to determine if the tachyarrhythmia episode is PT or MT. A first beat of the tachyarrhythmia is detected and the beat waveform is used to form a first template. A subsequently detected beat is detected and is compared to the first template. If the morphology of the subsequently detected beat is sufficiently similar to the first template, the waveform of the subsequently detected beat is used to update the first template. If the morphology of the subsequently detected beat is not similar to the first template, then the subsequently detected beat if used to form a new template.

Additional beats 245 are compared to the templates formed by previous beats of the tachyarrhythmia episode to determine if the morphologies of the additional beats meet 220 similarity requirements indicating consistency with any of the templates. If the morphology of a particular beat is similar to an existing template formed using one or more previous beats of the tachyarrhythmia episode, the particular beat is used to update 230 the template. If the morphology of a particular beat is not similar to any of the existing templates formed by previous beats of the tachyarrhythmia episode, a new template is formed 240 from the particular beat. If the morphology of a particular beat is similar to two or more existing templates, each formed using one or more previous beats of the tachyarrhythmia episode, a new template is formed 240 from the particular beat and all previous beats used to form the two or more existing templates. The two or more existing templates are erased. After a sufficient number of beats have been detected 235, the tachyarrhythmia episode is determined to be 250 MT or PT based on the templates.

In accordance with the embodiments of the invention, PT/MT discrimination and/or formation of a template characterizing a MT episode may be automatically acquired by an implantable cardiac rhythm management device. PT/Mt discrimination and/or formation of the template characterizing an MT episode may be performed either beat-by-beat while the tachyarrhythmia episode is in progress, or off-line, after the tachyarrhythmia episode has terminated. Furthermore, in the case that an initial tachyarrhythmia discrimination algorithm has classified the tachyarrhythmia episode as VT or SVT the processes described herein may be used to confirm the VT or SVT classification.

PT/MT discrimination may be used to enhance selection of an appropriate therapy to treat the tachyarrhythmia episode. If the tachyarrhythmia episode is determined to be PT, a more aggressive therapy may be selected. A therapy used to treat the PT may be selected based on a history of success of the therapy at terminating the PT. MT episodes that exhibit stable, consistent morphology may be classified according to MT type based on the characteristic morphology. This classification could be done by comparing the MT episodes to templates generated from previous MT episodes in accordance with embodiments of the invention. Particular therapy regimens may be associated with particular types of MT based on a historical success of the therapy regimens at treating the particular types of MT and also on other factors associated with the therapy regimens. Therapy regimens incorporating initial application of ATP may be used for tachyarrhythmia episodes classified as MT, while shocks may be reserved for tachyarrhythmia episodes classified as PT. The process may be adaptable, learning which therapies are most effective at treating particular types of tachyarrhythmia. Classification by MT type allows appropriate selection of therapy for treating particular types of MT, providing the capability to deliver less painful therapy. In addition, delivery of therapy based on PT/MT discrimination and MT tachyarrhythmia classification achieved via morphological analysis provides for therapy decisions based on morphological organization of the arrhythmia episodes rather than rate zone. This allows delivery of therapies that are more effective at treating specific types of arrhythmias which happen to fall into the same rate zone, but are morphologically distinct from each other and respond differently to different therapies.

As previously described, implementation of PT/MT discrimination in accordance with methods of the present invention may also be used to confirm the classification of VT or SVT. For example, if an SVT/VT algorithm classifies the tachyarrhythmia episode as SVT while the PT/MT discrimination processes of the present invention determines that cardiac beats of the tachyarrhythmia episode exhibit disorganized, inconsistent morphology, the tachyarrhythmia episode may be reclassified as VT, and more specifically as PVT. Confirmation of the SVT/VT determination may increase the SVT/VT discrimination sensitivity with no change in specificity. This confirmation may classify SVT with beat by beat morphology variation due to bundle branch block as PVT. Implementation of the PT/MT discrimination processes of the present invention, for confirmation of SVT/VT classification or for other purposes, may be selectable by a physician.

Figure 3B:
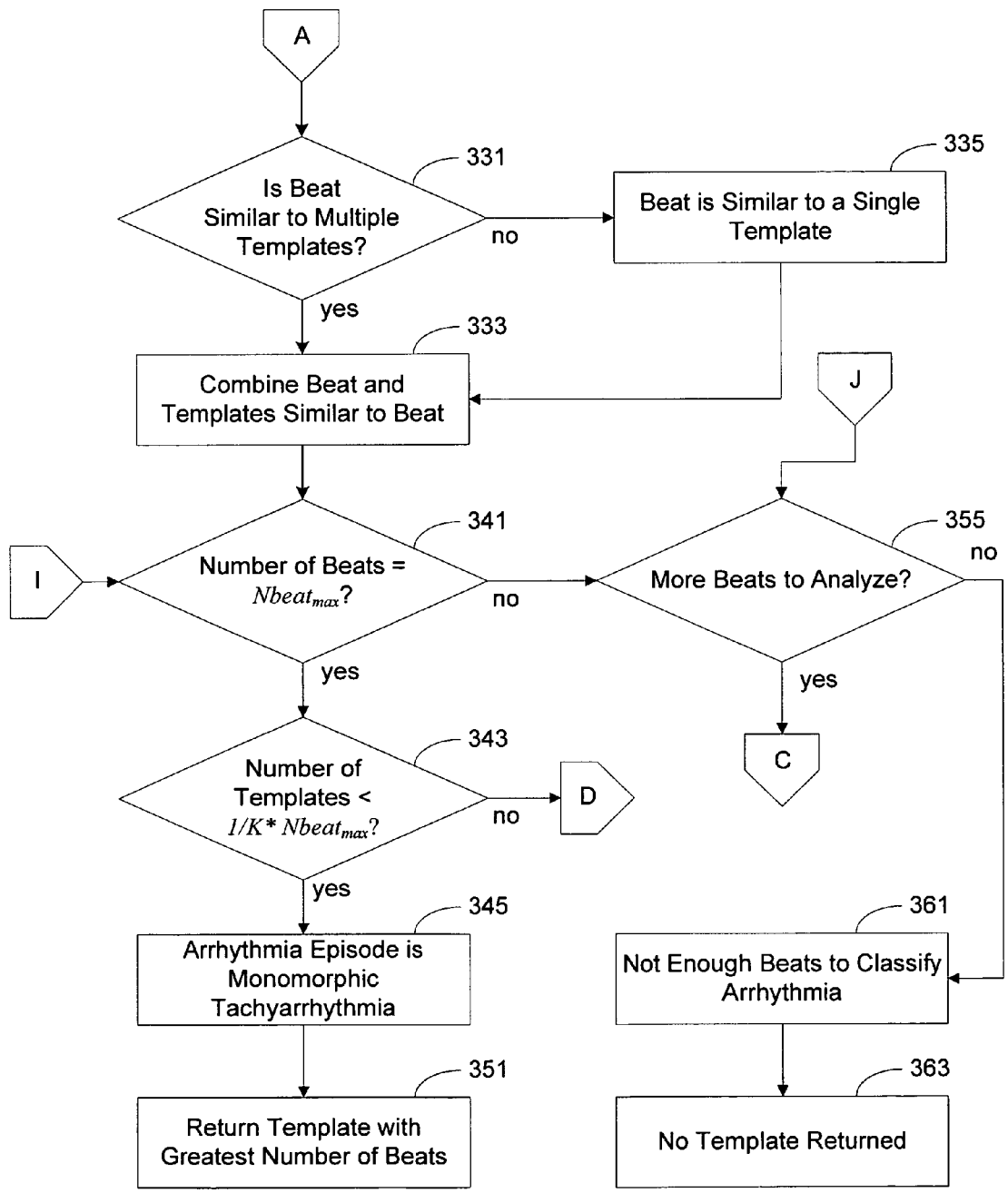
Figure 3C:
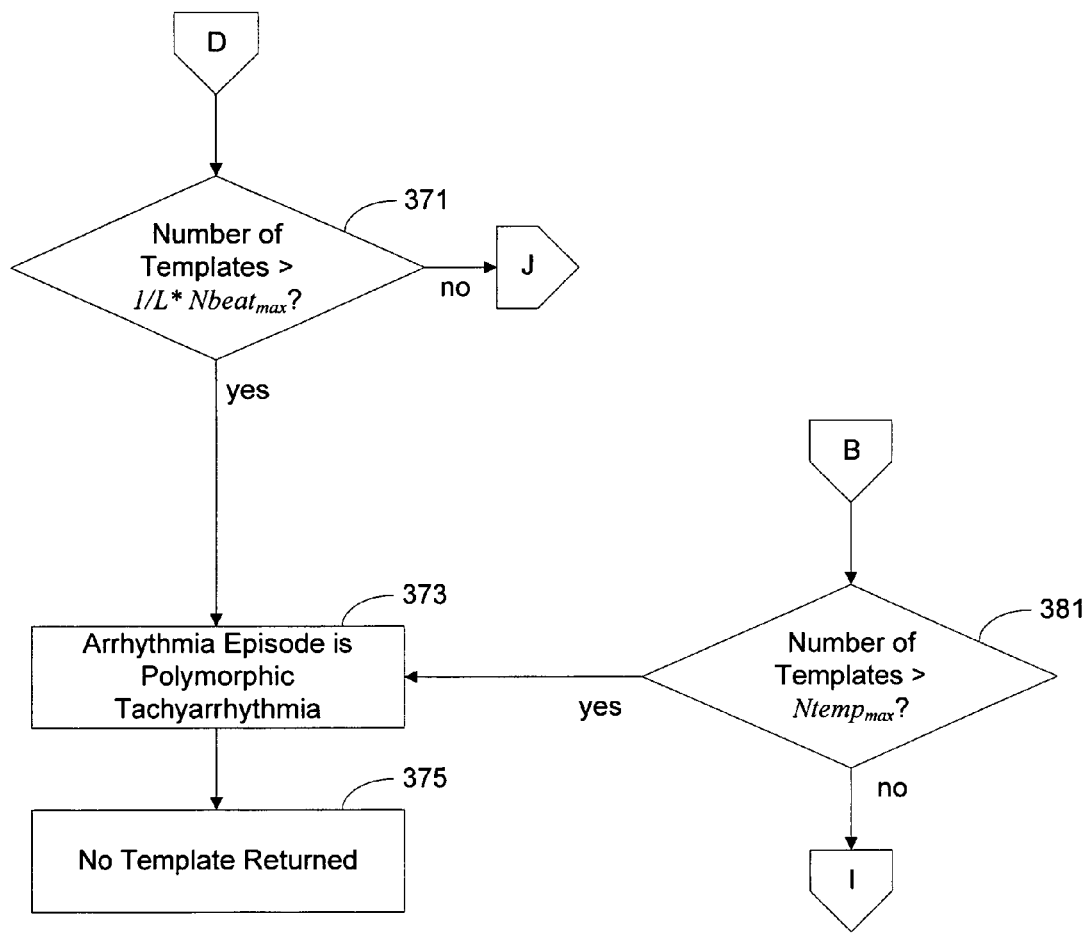

FIGS. 3A-3C provide a flowchart illustrating the PT/MT discrimination processes in accordance with embodiments of the invention. An arrhythmia episode is detected 301, such as by determining the rate of an initial number of beats, e.g., about three beats, of the arrhythmia episode. A first template is formed 305 using features extracted 303 from the waveform of the first beat after the tachyarrhythmia episode has been declared. In some embodiments, the feature extraction and template formation may involve two channels, such as extracting a fiducial point of a rate channel and the timings and amplitudes of a number of points found on a shock channel, as more specifically described in commonly owned U.S. Pat. No. 6,449,503 which is incorporated herein by reference. In some embodiments, feature extraction and template formation may involve calculating the area under sections of the shock or rate channel waveform, or calculating the coefficients of the Fourier or wavelet decomposition of the shock and/or rate channel waveform. In yet other embodiments, feature extraction, template formation and/or similarity determination may be based on the use of entropy measures to analyze the morphological complexity of the electrogram signal by cycle length irregularities and/or morphological complexity as described in commonly owned U.S. patent application Ser. No. 11/151,102 which is incorporated herein by reference. In still further embodiments, feature extraction, template formation and/or similarity determination may be based on morphological regularity measures such as those described in commonly owned U.S. patent application Ser. No. 11/038,996 which is incorporated herein by reference.

The second beat is detected and features of the second beat are extracted 311. Features of the beat are compared 313 to previously formed templates, e.g., by calculating a similarity measure XsimA. In one embodiment, the similarity measure is a correlation coefficient determined as described in previously incorporated U.S. Pat. No. 6,449,503. In other embodiments, the similarity measure is directly or indirectly proportional to the sum of the absolute value of the differences between corresponding features of the beat and the previously formed template.

The similarity measure is compared to a pre-determined threshold Tsim. If the similarity measure is greater than or equal to threshold (if XsimA≧Tsim), then the beat is similar to the template. If so, the first template is reformed by combining the shock channel waveforms of the current beat (in this case, the second beat) and all beats used to generate the first template (in this case, the first beat). In one embodiment, the template can be reformed by averaging the shock channel waveforms of the first and second beats. The characteristics of the template formed by combining the first template and the second beat are extracted.

If the similarity measure is less than threshold (if XsimA<Tsim), then the second beat is different from the first template. Therefore, the first template is unchanged and a second template is formed using the second beat.

A next beat is detected and features are extracted 311 from the next beat. The similarity between the beat and each previously formed template is determined 313, 315, 321.

If the similarity measures between the beat and all templates are less than threshold Tsim, then the beat is not similar 323 to any of the templates. Therefore, the templates are left unchanged and a new template is formed 325 using the beat.

If the similarity measures between the beat and multiple templates are greater than or equal to threshold Tsim, then the beat is similar 331 to the multiple templates. Therefore, a new template is formed 333 from the all the beats used to form the multiple templates. If the similarity measure between the beat and a single template is greater than or equal to threshold Tsim, the beat is similar 335 to the single template. The beat is combined 333 with the beats used to form the single template.

The process described above continues until the number of beats analyzed reaches 341 a predetermined number, $Nbeat_{max}$, until the number of templates formed is greater than 381 a predetermined number $Ntemp_{max}$, or until there are 355 no more beats to analyze. If a sufficient number of beats, $Nbeat_{max}$, are not available 361 for analysis, then no template is returned 363 from the process.

If a pre-determined number of templates, $Ntemp_{max}$, have been formed 381, then the beats are not consistent in morphology. Therefore, the arrhythmia episode is determined to be 373 a PT and no template is returned 375 from the process.

If a pre-determined number of beats, $Nbeat_{max}$, have been analyzed 341, the number of templates formed, Ntemp, is determined. If the number of templates formed is less than 343 a pre-determined fraction (1/K), where K is in a range of about 1 to about 5, times the number of analyzed beats, $Ntemp<(1/K)*Nbeat_{max}$, then the beats are consistent in morphology. The arrhythmia episode is determined to be 345 a MT. The template created from the largest number of beats is returned 351 from the process. The template returned from the process may be used, for example, to identify subsequently detected arrhythmias as being associated with particular monomorphic arrhythmia types. In some embodiments, a therapy may be selected to treat a tachyarrhythmia episode based on monomorphic arrhythmia type, and more specifically, based on the historical success of the therapy at mitigating the monomorphic arrhythmia type, and/or satisfaction with the therapy based on success as well as other factors.

If the number of templates is greater than or equal to 371 a pre-determined fraction (1/L), where L is in a range of about 1 to about 5, times the number of analyzed beats, $Ntemp≧(1/L)*Nbeat_{max}$, then the beats are not consistent in morphology. The episode is determined to be 373 a PT and no template is returned 375 from the process.

Figure 4:
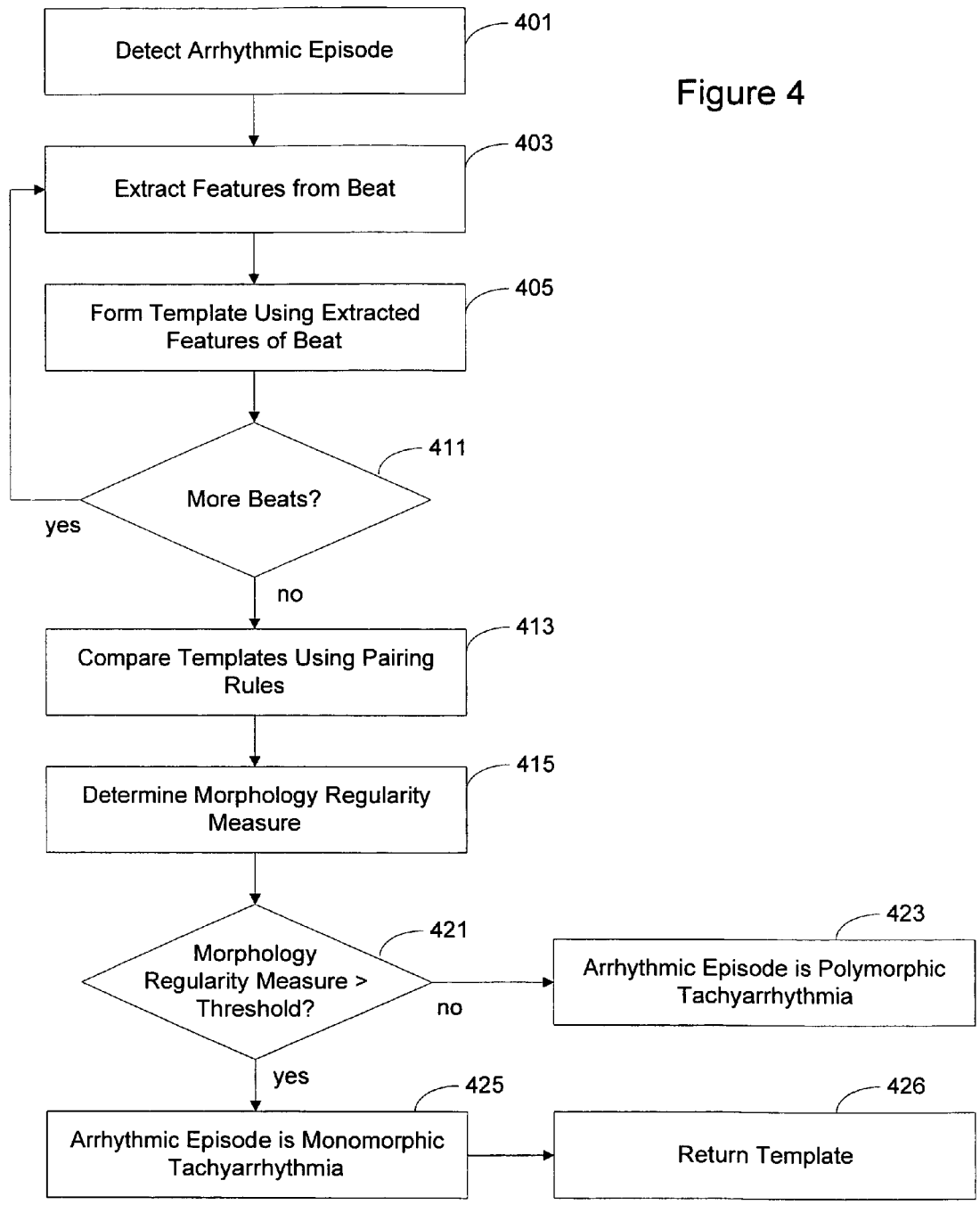
FIG. 4 is a flowchart illustrating a method for identifying similarities between templates using a pairing rule to determine which templates should be compared and for discriminating polymorphic tachyarrhythmia from monomorphic tachyarrhythmia in accordance with embodiments of the invention.

Another embodiment of the invention involves determining similarities between templates using a pairing rule to determine which templates should be compared. A method in accordance with this embodiment is illustrated in the flowchart of FIG. 4. During a tachyarrhythmia episode 401, a set of beats $B_1 \ldots B_{Nbeat}$ is collected during a beat window. For each beat 411 in the beat window, a rudimentary (non-averaged) template is formed by extracting 403 features of the beat waveform, resulting in formation of 405 templates $T_1 \ldots T_{Nbeat}$. In one implementation, feature extraction and template formation may involve two channels, such as extracting a fiducial point of a rate channel and the timings and amplitudes of a number of points found on a shock channel, as more specifically described in commonly owned U.S. Pat. No. 6,449,503 which is incorporated herein.

The templates are compared to each other by using 413 a pairing rule. For example, template Tn is compared to Tm by calculating a similarity measure S(Tn,Tm), n≠m. In one embodiment, the similarity measure is a correlation coefficient determined as described in previously incorporated U.S. Pat. No. 6,449,503. In other embodiments, the similarity measure is directly or indirectly proportional to the sum of the absolute value of differences between corresponding features of the beat and the previously formed template. The similarity measure is compared to a predetermined threshold Tsim, so that similarity $C_i$ is established for the $i^{th}$ pairing if $S_i \geq T_{sim}$. The pairing rule determines the total number of comparisons Ncomp from which arise the set of comparisons results $C_i \ldots C_{Ncomp}$. In one embodiment, the pairing rule may be that of simple adjacency, $1 \leq n=m-1 \leq Nbeat$, resulting in Ncomp=Nbeat−1. In another embodiment, the pairing rule may be to compare the most recent template, $T_{Nbeat}$, to every other prior $T_N$ in the set, $1 \leq n \leq Nbeat$, again resulting in Ncomp=Nbeat−1. In yet another embodiment, the pairing rule may be that of comparing all possible pairwise combinations (Tn,Tm), over $1 \leq n \neq m \leq Nbeat$, resulting in Ncomp=Nbeat×(Nbeat−1)/2. Various pairing rules may be envisioned to take advantage of local beat-to-beat morphology characteristics on the scale of an adjacent beat pair or over a local beat window.

A morphology regularity measure is determined 415 based on the comparisons determined as discussed in the paragraph above. For a beat window of limited length, the latter rule provides the most available comparisons from which to form a morphology regularity measure. $C_i = 1$ is assigned if similarity between templates is established and $C_i = 0$ is assigned if similarity between templates is not established. In one embodiment, the morphology regularity measure is defined as $$M = \frac{\sum_i C_i}{Ncomp},$$

or the fraction of the total number of morphology comparisons where the morphologies are considered to be similar. The morphology regularity measure is compared 421 to a threshold, Treg, so that morphology regularity is established if $M \geq Treg$.

In another embodiment, we define a morphology regularity measure, M, as an estimate of a central value over the similarity measure $S_i$, where the central value may be an average estimated, for example, from an arithmetic or geometric mean, a p-norm, a median, mode, minimum, maximum, or other value. The morphology regularity measure, M, is compared to a predetermined threshold Treg, so that the morphology regularity is established if $M \geq Treg$. In another embodiment, we define a morphology regularity measure, M, as the variability of the similarity measures $S_i$ about a central value $V_c$ that may be arbitrarily predetermined or established from the $S_i$ as in the previous embodiment description. The variability is then defined as $M = \Sigma_i |S_i - V_c|^p$ with p an arbitrary power, or as $M = \max(|S_i - V_c|)$. In this embodiment, M is compared to a predetermined threshold, Treg, so that morphology regularity is asserted if $M \geq Treg$.

In one embodiment, a trend of morphology regularity or irregularity may be established by performing Nreg morphology regularity measurements on either overlapping or disjoint beat windows, yielding the set of measurements $M_1 \ldots M_{reg}$. Again, several embodiments may be envisioned treating the collection of the $M_j$ in similar fashion to the $S_i$ example to confirm a trend of morphology regularity or irregularity.

If the morphology regularity, or a trend of morphology regularity, is established 421, then the tachyarrhythmia episode is determined to be 425 a MT and an MT template is returned 426. If irregularity is established, the tachyarrhythmia episode is determined to be 423 a PT.

The pairing rule algorithm may be combined with the algorithm described in connection with FIGS. 3A-3C for returning an MT template. During the template comparisons, if two templates, $T_n$ and $T_m$ are found to be similar, i.e., $S(T_n,T_m) \geq Tsim$, then these two templates may be combined into a new template, for example, by averaging of corresponding feature points. The new template then replaces the two former templates requiring comparison, and provides a means of storing an MT template if morphology regularity is established. For example, the template formed from the largest number of beats may be used as the best candidate MT template. In the event of a tie, no templates could be returned, or all could be returned as multiple candidate templates.

Figure 5A:
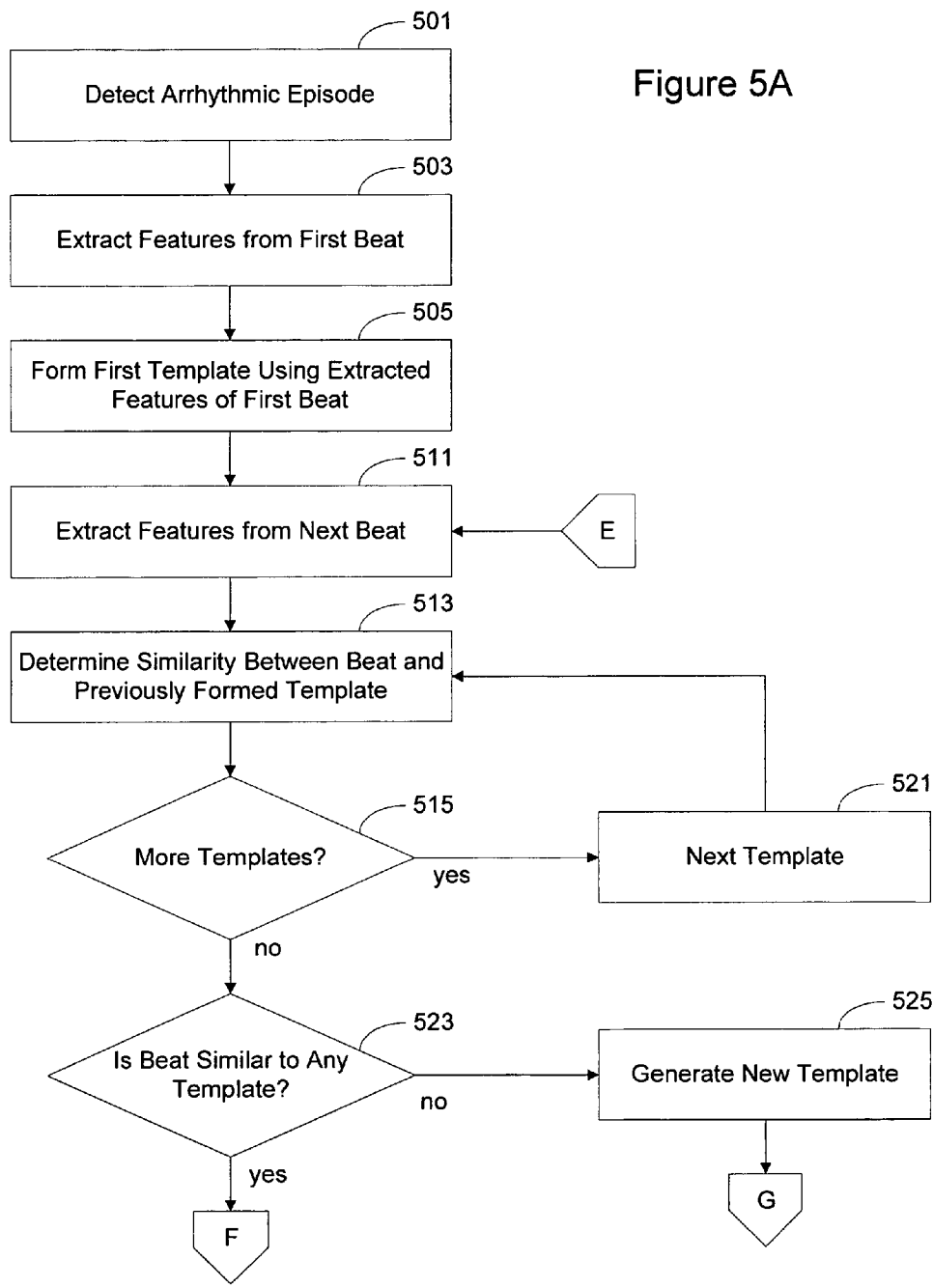
FIGS. 5A-5C provide a flowchart illustrating a method for polymorphic tachyarrhythmia/monomorphic tachyarrhythmia discrimination and for forming tachyarrhythmia templates using a pairing rule in accordance with embodiments of the invention.
Figure 5B:
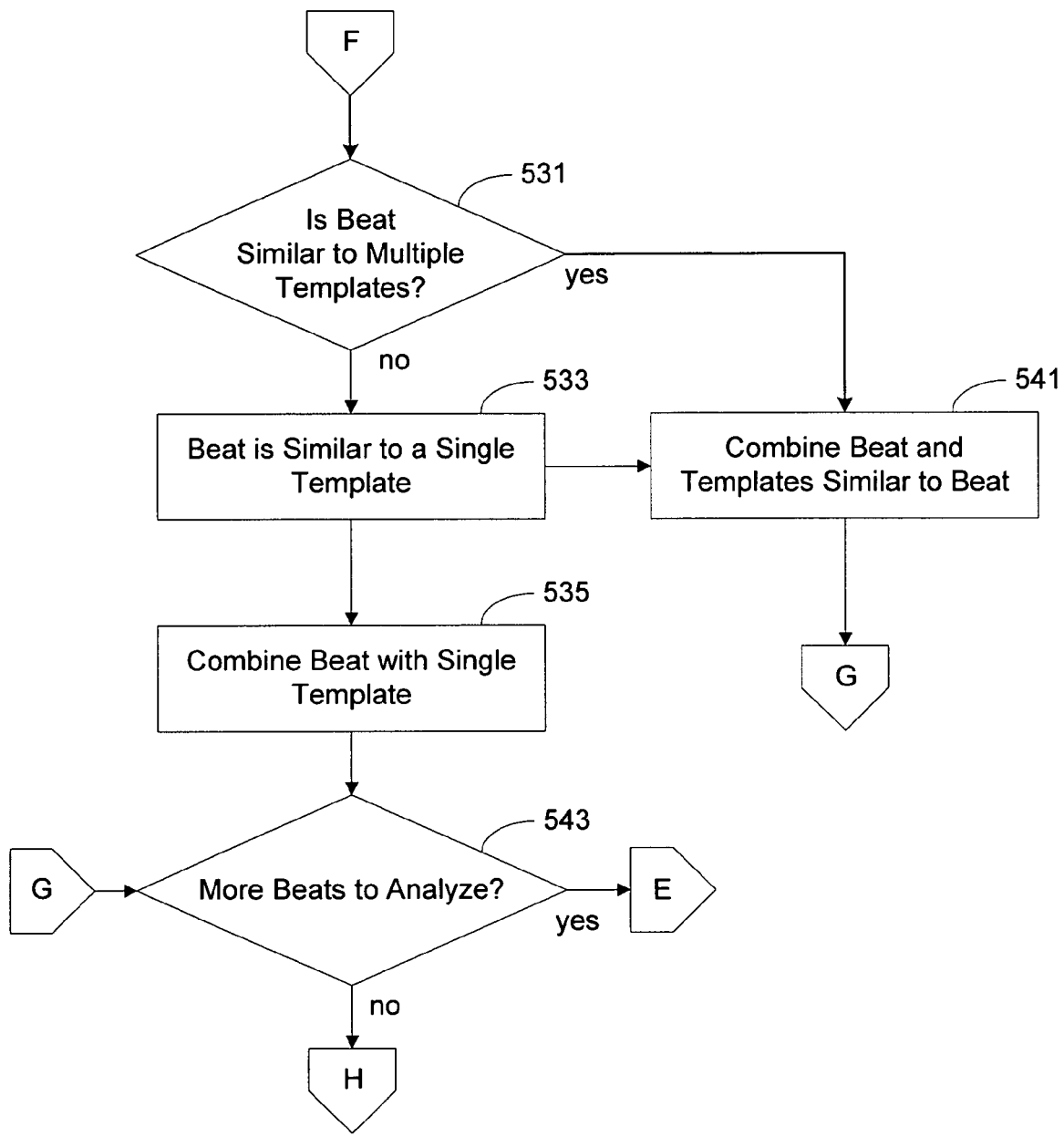
Figure 5C:
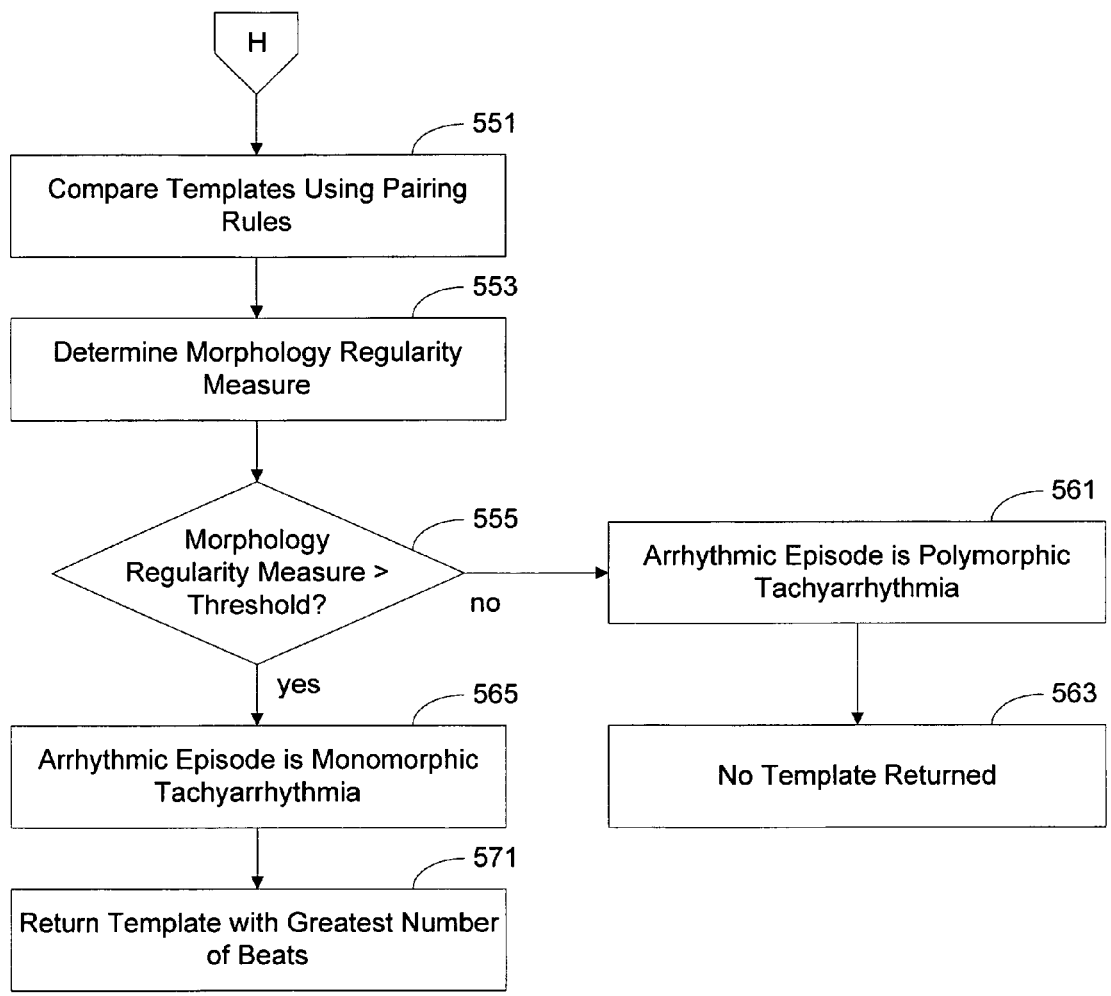

FIGS. 5A-5C illustrate a method for PT/MT discrimination and for forming MT templates in accordance with embodiments of the invention. An arrhythmia episode is detected 501, such as by determining the rate of an initial number of beats, e.g., about three beats, of the arrhythmia episode. A first template is formed 505 using features extracted 503 from the waveform of the first beat after the tachyarrhythmia episode has been declared.

The second beat is detected and features of the second beat are extracted 511. Features of the beat are compared 513 to previously formed templates, e.g., by calculating a similarity measure XsimA. The similarity measure is compared to a pre-determined threshold Tsim. If the similarity measure is greater than or equal to threshold (if XsimA≥Tsim), then the beat is similar to the template. If so, the first template is updated using the waveforms of the current beat (in this case, the second beat) and all beats used to generate the first template (in this case, the first beat). The characteristics of the representative waveform formed by combining the first template and the second beat are extracted.

If the similarity measure is less than threshold (if XsimA<Tsim), then the second beat is different from the first template. Therefore, the first template is unchanged and a second template 525 is formed using the second beat.

A next beat is detected and features are extracted 511 from the next beat. The similarity between the beat and each previously formed template is determined 513, 515, 521.

If the similarity measures between the beat and all templates are less than threshold Tsim, then the beat is not similar 523 to any of the templates. Therefore, the previous templates are unchanged and a new template is formed 525 using the beat.

If the similarity measures between the beat and multiple are greater than or equal to threshold Tsim, then the beat is similar 531 to the multiple templates. Therefore, a new template is formed 541 from the current beat and all previous beats used to generate the multiple templates. If the similarity measure between the beat and a single template is greater than or equal to threshold Tsim, the beat is similar 533 to the single template. The beat is combined 535 with the beats used to form the single template.

The process described above continues 543 until the all the beats in the beat window are analyzed.

The templates are compared using 551 a pairing rule as previously discussed. A morphology regularity measure, M, is determined 553 based on the comparisons. The morphology regularity measure, M, is compared 555 to a threshold, Treg, so that morphology regularity is established if $M \geq Treg$. If the morphology regularity, or a trend of morphology regularity, is established 555, then the tachyarrhythmia episode is determined to be 565 a MT and the template formed using the greatest number of beats is returned 571 by the process. If irregularity is established, the tachyarrhythmia episode is determined to be 561 a PT and no template is returned 563.

Figure 6:
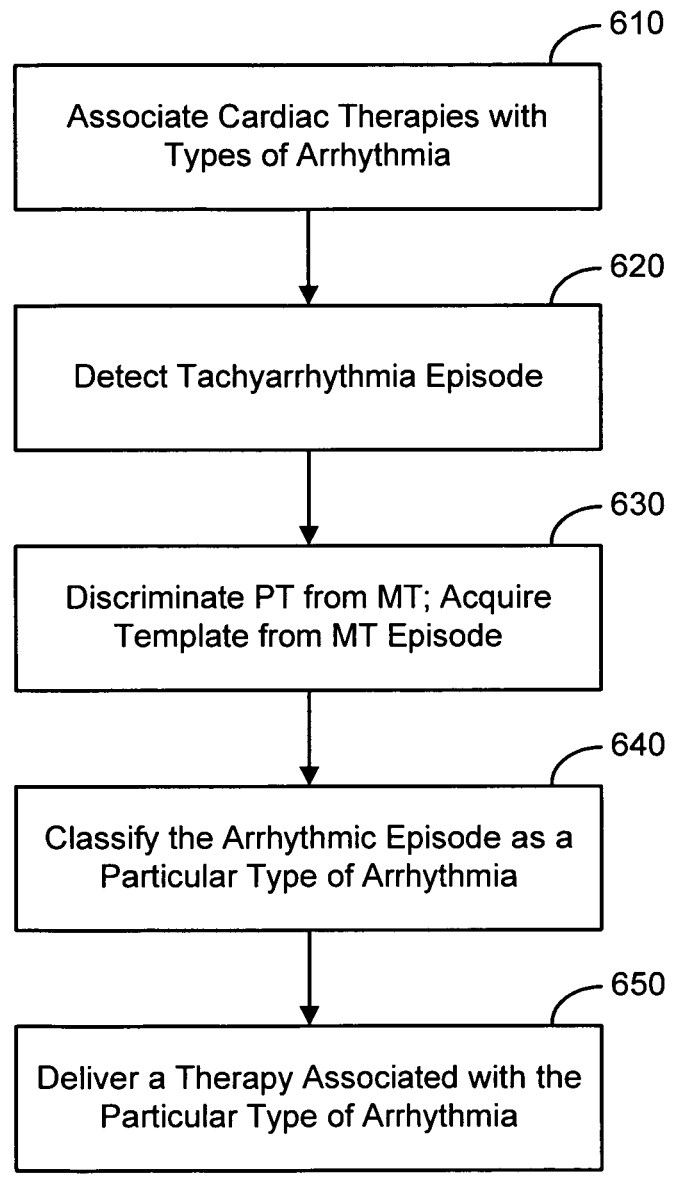
FIG. 6 illustrates a method of delivering cardiac therapy to a patient based on the morphological regularity of the arrhythmia episode and/or the type of monomorphic tachyarrhythmia in accordance with embodiments of the invention.

FIG. 6 illustrates a method of delivering cardiac therapy to a patient in accordance with embodiments of the invention. Various cardiac therapies are respectively associated 610 with types of arrhythmia. A representative set of cardiac therapies may involve, for example, anti-tachycardia pacing (ATP) including burst pacing, (e.g., pacing at 25 Hz or 50 Hz sequences), ramp pacing (e.g., burst pacing with each pace-to-pace interval shortened), scan pacing (e.g., burst pacing with the burst cycle length of each burst shortened between successive bursts, cardioversion shocks (e.g., cardioversion shocks delivered at about 0.1 Joules to about 31 Joules), and titration of defibrillation shocks.

Cardiac beats of a tachyarrhythmia episode are detected 620. A template is acquired 630 from the tachyarrhythmia episode if the tachyarrhythmia episode is determined to be an MT episode. The template is compared to one or more representative beat morphologies associated with various types of arrhythmia. The tachyarrhythmia episode is classified 640 as a particular type of arrhythmia based on the comparison. A therapy associated with the particular type of arrhythmia is delivered 650 to the patient. For example, discrimination of PT/MT and acquisition of the template 630 may be performed using one of the methods described above in connection with FIGS. 1-5 above.

Still referring to FIG. 6, as an example, useful for illustrative purposes but not limiting, consider that a current episode template returned by the process corresponds to at least one of the representative beat morphologies indicating that the episode is a known type of arrhythmia. Correspondence to the representative beat morphology (e.g., template) of the known type of arrhythmia may be determined by, for example, correlation, convolution, and/or statistical analysis of cardiac waveform information. The representative beat morphology of the known type of arrhythmia may be associated with treatment history and outcome information. If a previous therapy was satisfactory, for example, if information associated with the known type of arrhythmia indicates that ATP was satisfactory in treating the last tachyarrhythmia episode of the known type, then the previous therapy may be delivered again if the known type of arrhythmia is detected.

If the previous therapy attempt was not satisfactory, for example, if the information associated with the known type of arrhythmia indicates that ATP was not satisfactory in treating the last tachyarrhythmia of that type, or if the previous therapy accelerated the cardiac rhythm, then a different and/or more aggressive therapy may be delivered. If no representative beat morphologies associated with various types of arrhythmia are found to correspond to the current episode template, then a new representative beat morphology may be created based on the current episode template. Whether or not a particular therapy was satisfactory may be based upon one or more of a variety of factors, including: if the therapy was effective, if the therapy did not take too long, if the therapy did not cause unnecessary pain, if the therapy did not require unnecessary energy, if the physician deemed the therapy to be successful or satisfactory, and/or other subjective and/or objective factors. Selection of therapy based on a history of success or satisfaction associated with the therapy is described in commonly owned U.S. Pat. No. 6,400,986, U.S. Patent Application Publication 2003/0120316, and U.S. patent applications, Ser. No. 10/995,655, filed Nov. 23, 2004, Ser. No. 10/995,704, filed Nov. 23, 2004, and U.S. Ser. No. 10/955,831, filed Sep. 30, 2004 all of which are incorporated herein by reference. Methods of determining morphological organization of arrhythmias and selection of therapy based on morphological organization and/or history of satisfaction, aspects of which may be used in conjunction with the embodiments provided herein, are described in commonly owned U.S. patent application Ser. No. 11/209,976, filed Aug. 23, 2005 which is incorporated herein by reference.

Figure 7:
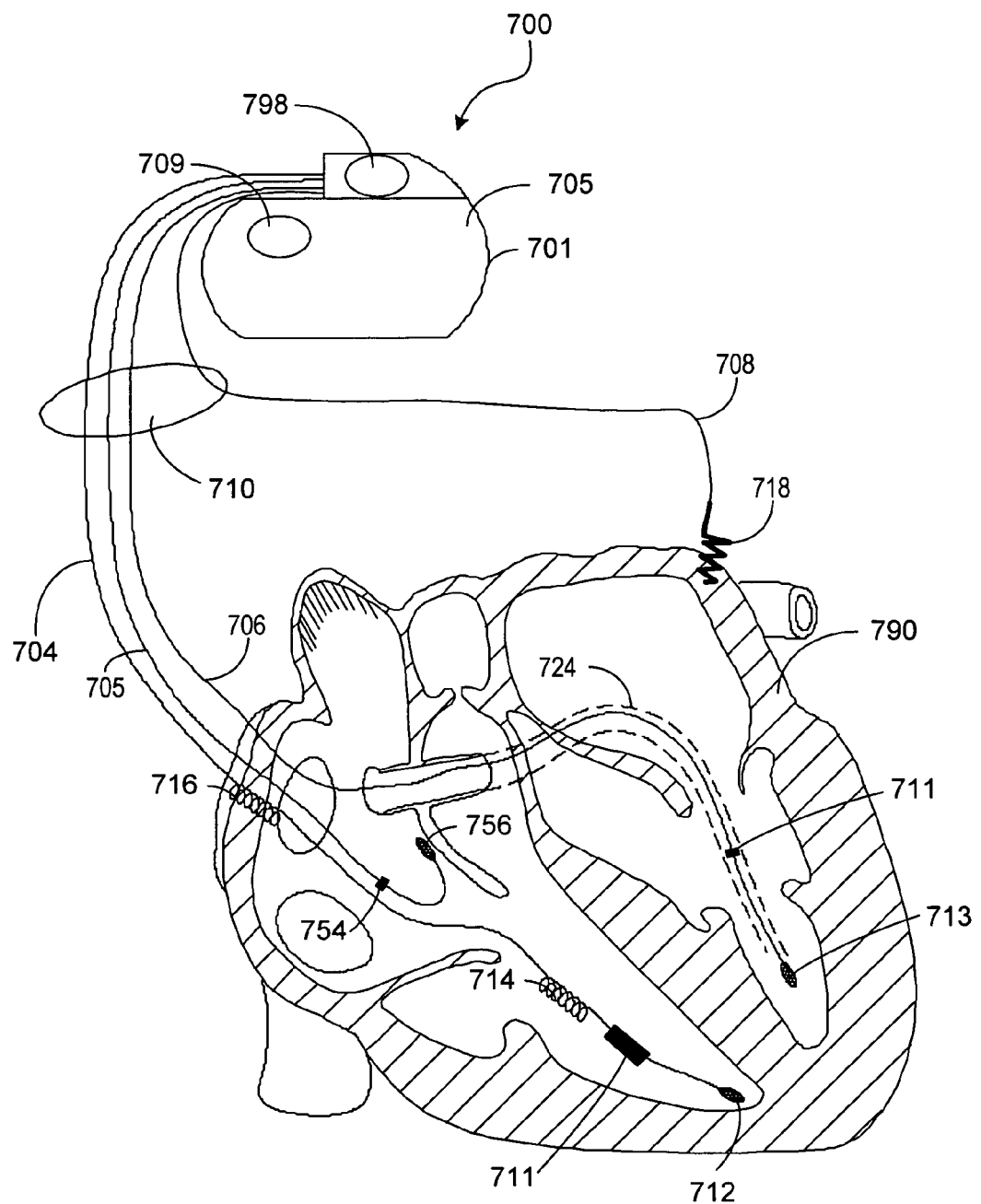
FIG. 7 is a partial view of one embodiment of an implantable medical device that may be used to implement discriminating between monomorphic and polymorphic ventricular tachyarrhythmia using template generation in accordance with embodiments of the invention.

Referring now to FIG. 7 of the drawings, there is shown one embodiment of a cardiac rhythm management system that may be used to implement discrimination of MT and PT using template generation in accordance with the present invention. The cardiac rhythm management system in FIG. 7 includes a patient implantable medical device (PIMD) 700 electrically and physically coupled to a lead system 710. The housing and/or header of the PIMD 700 may incorporate one or more electrodes 798, 709 used to provide electrical stimulation energy to the heart and to sense cardiac electrical activity. The PIMD 700 may utilize all or a portion of the PIMD housing as a can electrode 709. The PIMD 700 may include an indifferent electrode 798 positioned, for example, on the header or the housing of the PIMD 700. If the PIMD 500 includes both a can electrode 709 and an indifferent electrode 798, the electrodes 798, 709 typically are electrically isolated from each other.

The lead system 710 is used to detect electric cardiac signals produced by the heart 790 and to provide electrical energy to the heart 790 under certain predetermined conditions to treat cardiac arrhythmias. The lead system 710 may include one or more electrodes used for pacing, sensing, and/or defibrillation. In the embodiment shown in FIG. 7, the lead system 710 includes an intracardiac right ventricular (RV) lead system 704, an intracardiac right atrial (RA) lead system 705, an transvenous left ventricular (LV) lead system 706, and an extracardiac left atrial (LA) lead system 708. The lead system 710 of FIG. 7 illustrates one embodiment that may be used in connection with the tachyarrhythmia therapy selection methodologies described herein. Other leads and/or electrodes may additionally or alternatively be used.

The lead system 710 may include leads 704, 705, 706 implanted in a human body with portions of the leads 704, 705, 706 inserted into a heart 790. The leads 704, 705, 706 include various electrodes positionable in relation to the heart for sensing electrical activity of the heart and for delivering electrical stimulation energy to the heart, for example, pacing pulses and/or defibrillation shocks to treat various arrhythmias of the heart.

As illustrated in FIG. 7, the lead system 710 may include one or more extracardiac leads 708 having electrodes, e.g., epicardial electrodes, positioned at locations outside the heart for sensing and/or pacing one or more heart chambers.

The right ventricular lead system 704 illustrated in FIG. 7 includes an SVC-coil 716, an RV-coil 714, an RV-ring electrode 711, and an RV-tip electrode 712. The right ventricular lead system 704 extends through the right atrium 720 and into the right ventricle 719. In particular, the RV-tip electrode 712, RV-ring electrode 711, and RV-coil electrode 714 are positioned at appropriate locations within the right ventricle for sensing and delivering electrical stimulation pulses to the heart. The SVC-coil 716 is positioned at an appropriate location within the right atrium chamber of the heart 790 or a major vein leading to the right atrial chamber of the heart 790.

In one configuration, the RV-tip electrode 712 referenced to the can electrode 709 may be used to implement unipolar pacing and/or sensing in the right ventricle. Bipolar pacing and/or sensing in the right ventricle may be implemented using the RV-tip 712 and RV-ring 711 electrodes.

In yet another configuration, the RV-ring 711 electrode may optionally be omitted, and bipolar pacing and/or sensing may be accomplished using the RV-tip electrode 712 and the RV-coil 714, for example. The right ventricular lead system 704 may be configured as an integrated bipolar pace/shock lead. The RV-coil 714 and the SVC-coil 716 are defibrillation electrodes.

The left ventricular lead 706 includes an LV distal electrode 713 and an LV proximal electrode 717 located at appropriate locations in or about the left ventricle for pacing and/or sensing the left ventricle. The left ventricular lead 706 may be guided into the right atrium of the heart via the superior vena cava. From the right atrium, the left ventricular lead 706 may be deployed into the coronary sinus ostium, the opening of the coronary sinus. The lead 706 may be guided through the coronary sinus to a coronary vein 724 of the left ventricle. This vein is used as an access pathway for leads to reach the surfaces of the left ventricle that are not directly accessible from the right side of the heart. Lead placement for the left ventricular lead 706 may be achieved via subclavian vein access and a preformed guiding catheter for insertion of the LV electrodes 713, 717 adjacent to the left ventricle.

Unipolar pacing and/or sensing in the left ventricle may be implemented, for example, using the LV distal electrode 713 referenced to the can electrode 509. The LV distal electrode 713 and the LV proximal electrode 717 may be used together as bipolar sense and/or pace electrodes for the left ventricle. The left ventricular lead 706 and the right ventricular lead 704, in conjunction with the PIMD 700, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 705 includes a RA-tip electrode 556 and an RA-ring electrode 754 positioned at appropriate locations in the right atrium for sensing and pacing the right atrium. In one configuration, the RA-tip 756 referenced to the can electrode 709, for example, may be used to provide unipolar pacing and/or sensing in the right atrium 720. In another configuration, the RA-tip electrode 756 and the RA-ring electrode 754 may be used to effect bipolar pacing and/or sensing.

FIG. 7 illustrates one embodiment of a left atrial lead system 708. In this example, the left atrial lead 708 is implemented as an extracardiac lead with an LA distal electrode 718 positioned at an appropriate location outside the heart 790 for sensing and pacing the left atrium. Unipolar pacing and/or sensing of the left atrium may be accomplished, for example, using the LA distal electrode 718 to the can 709 pacing vector. The left atrial lead 708 may be provided with additional electrodes used to implement bipolar pacing and/or sensing of the left atrium.

Figure 8:
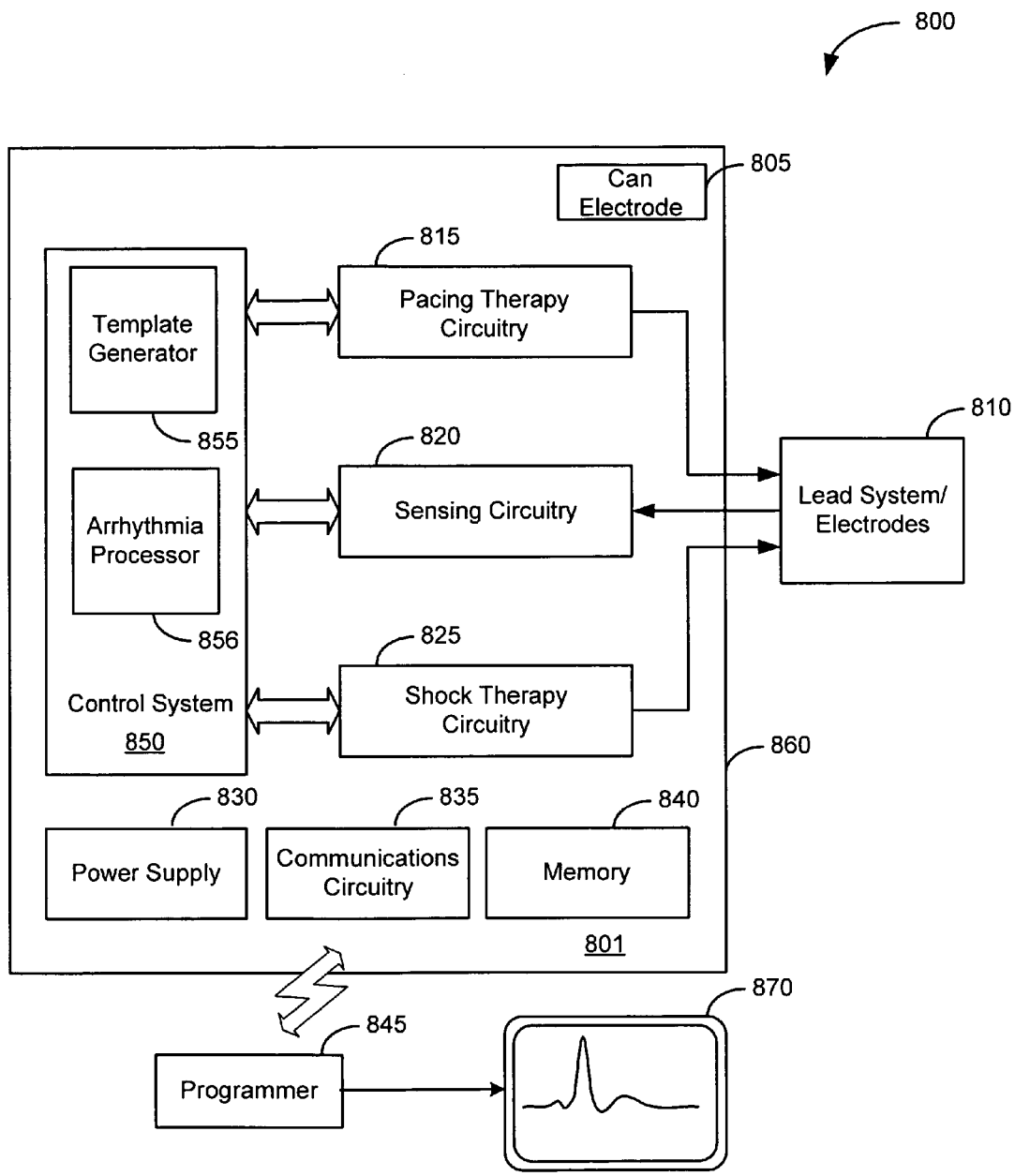
FIG. 8 is a block diagram illustrating functional components of an implantable medical device with which discrimination between monomorphic and polymorphic ventricular tachyarrhythmia using template generation may be implemented in accordance with embodiments of the present invention.

Referring now to FIG. 8, there is shown a block diagram of an embodiment of a CRM system 800 employing a PIMD 860 suitable for implementing arrhythmia discrimination and therapy selection methodologies of the present invention. FIG. 8 shows the CRM system 800 divided into functional blocks. There exist many possible configurations in which these functional blocks can be arranged. The example depicted in FIG. 8 is one possible functional arrangement. The CRM system 800 includes circuitry for receiving cardiac signals from a heart and delivering electrical energy in the form of pace pulses or cardioversion/defibrillation pulses to the heart.

A cardiac lead system 810 may be implanted so that cardiac electrodes contact heart tissue as described above in connection with FIG. 8. The cardiac electrodes of the lead system 810 sense cardiac signals associated with electrical activity of the heart. The sensed cardiac signals may be transmitted to a PIMD 860 through the lead system 810. The cardiac electrodes and lead system 810 may be used to deliver electrical stimulation generated by the PIMD 860 to the heart to mitigate various cardiac arrhythmias. The PIMD 660, in combination with the cardiac electrodes and lead system 810, may detect cardiac signals and deliver therapeutic electrical stimulation to any of the left and right ventricles and left and right atria, for example. A can electrode 805 coupled to a housing of the PIMD 860 may additionally be used to sense cardiac signals and deliver electrical stimulation to the heart.

In one embodiment, PIMD circuitry 801 is encased in a hermetically sealed housing suitable for implanting in a human body. Power is supplied by an electrochemical battery 830 that is housed within the PIMD 860. In one embodiment, the PIMD circuitry 801 is a programmable microprocessor-based system, including a control system 850, sensing circuit 820, pacing therapy circuit 815, shock therapy circuit 825, and memory 840. The memory 840 may be used, for example, to store template information, representative beat morphologies associated with various arrhythmia types, parameters for various pacing and defibrillation therapy regimens, information related to historical satisfaction with various therapies, and data associated with sensed cardiac signals or other information. The information stored in the memory 840 may be used on-board for various purposes and/or transmitted via telemetry to an external programmer unit 645 or other patient-external device, as desired.

Communications circuitry 835 allows the PIMD 860 to communicate with an external programmer unit 845 and/or other patient-external system(s). In one embodiment, the communications circuitry 835 and the programmer unit 845 use a wire loop antenna and a radio frequency telemetric link to receive and transmit signals and data between the programmer 845 and communications circuitry 835. In this manner, programming commands may be transferred to the PIMD 860 from the programmer 845 during and after implant. In addition, stored cardiac data may be transferred to the programmer unit 845 from the PIMD 860, for example.

Sensing circuitry 820 detects cardiac signals sensed at the cardiac electrodes 810. The sensing circuitry may include, for example, amplifiers, filters, A/D converters and other signal processing circuitry. Cardiac signals processed by the sensing circuitry may be communicated the control system 850 and to the template processor 855.

The control system 850 may used to control various subsystems of the PIMD 860, including the pacing therapy circuit 815, the shock therapy circuitry 825, and the sensing circuitry 820. The control system 850 may also include an arrhythmia processor 856 for discriminating between PT and MT and for recognizing various types of tachyarrhythmias as previously described herein. The control system may also include template generator 855 for implementing template initiation, template generation and template updating. The control system 850 may select therapy regimens to treat detected arrhythmias based on the PT/MT discrimination and/or identification of MT type and/or history of success or satisfaction with regard to particular therapy regimens delivered to treat the tachyarrhythmias.

The pacing therapy circuit 815 is controlled by a pacemaker in the control system 650 and may be used to deliver pacing stimulation pulses to the heart through one or more of the cardiac electrodes, according to a pre-established pacing regimen under appropriate conditions. Also, the pacing therapy circuit 815 may deliver ATP therapy in response to VTs that correspond to templates associated with ATP and/or in response to VTs that do not correspond to a template.

The shock therapy circuit 825 and pacing therapy circuit 815 are coupled to an arrhythmia processor 856 of the control system 850. The shock therapy circuit 825 may be used to deliver high-energy electrical stimulation to the heart to terminate or mitigate cardiac arrhythmias such as atrial or ventricular tachycardia or fibrillation detected or predicted by the control system 850 when patient history suggests that ATP is not effective and/or satisfactory, and/or when a template does not correspond to a cardiac episode.

The PIMD 860 may optionally be coupled to a display device 870 capable of displaying various information related to cardiac rhythm analysis using morphological templates, template creation and maintenance, and/or therapy selection, as well as other information. For example, the display device 870 may depict a graphical display of one or more detected cardiac waveforms along with the templates used to analyze or classify the detected cardiac waveforms. The display may show various data regarding the number of templates used by the PIMD, including, for example, statistics relating to the frequency particular templates were used to analyze or classify cardiac waveforms. The display device 870 provides a user interface allowing a physician or other person to select various features of the arrhythmia discrimination, template generation and/or therapy selection features described herein. Other uses for the display in connection with the template creation and therapy selection methods of the invention are also possible.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of arrhythmia discrimination for implementation by an implantable cardiac rhythm management device, comprising:
    detecting cardiac beats associated with an arrhythmia episode;
    forming a plurality of templates of the arrhythmia episode using morphological features of the cardiac beats of the arrhythmia episode, wherein forming the plurality of templates includes:
        forming at least one template of the arrhythmia episode;
        measuring similarity between morphological features of a cardiac beat of the arrhythmia episode and each previously formed template of the arrhythmia episode;
        using the cardiac beat to modify a previously formed template of the arrhythmia episode in response to a measure of similarity between the cardiac beat and the previously formed template being greater than a similarity threshold; and
        forming an additional template of the arrhythmia episode in response to measures of similarity between the cardiac beat and each previously formed template being less than a similarity threshold;
    determining the number of templates formed from the arrhythmia episode; and
    discriminating between monomorphic tachyarrhythmia and polymorphic tachyarrhythmia based on the number of templates determined to be formed using the cardiac beats of the arrhythmia episode.

2. The method of claim 1, wherein measuring the similarity between the morphological features of the cardiac beat and each previously formed template comprises:
    extracting a fiducial point from a rate channel signal of the cardiac beat;
    extracting a plurality of features from a shock channel signal of the cardiac beat; and
    determining a correlation coefficient between the shock channel features and each previously formed template.

3. The method of claim 1, further comprises using the discrimination between monomorphic and polymorphic tachyarrhythmia to reclassify a previously made ventricular tachyarrhythmia (VT) or supraventricular tachyarrhythmia (SVT) classification.

4. The method of claim 1, wherein using the cardiac beat to modify a previously formed template of the arrhythmia episode comprises averaging features of the cardiac beat and the previously formed template.

5. The method of claim 1, wherein forming the plurality of templates further comprises forming an additional template of the arrhythmia episode in response to measures of similarity between the cardiac beat and at least two previously formed template templates being greater than a similarity threshold.

6. The method of claim 5, further comprising erasing the at least two previously formed templates.

7. The method of claim 1, wherein discriminating between monomorphic tachyarrhythmia and polymorphic tachyarrhythmia comprises determining if the number of templates is greater then a predetermined fraction multiplied by the number of beats of the arrhythmia episode for which similarity was measured.

8. The method of claim 1, wherein at least one of forming the one or more templates and discriminating between monomorphic tachyarrhythmia and polymorphic tachyarrhythmia is performed during the arrhythmia episode.

9. The method of claim 1, further comprising:
    storing a particular template of the one or more templates, the particular template representative of the arrhythmia episode; and
    classifying a subsequent monomorphic tachyarrhythmia episode according to monomorphic arrhythmia type using the particular template.

10. The method of claim 1, further comprising confirming a determination of supraventricular tachyarrhythmia if the arrhythmia episode is determined to be monomorphic tachyarrhythmia based on the discrimination between monomorphic tachyarrhythmia and polymorphic tachyarrhythmia.

11. The method of claim 1, further comprising:
classifying the arrhythmia episode according to monomorphic arrhythmia type if the arrhythmia episode is determined to be monomorphic tachyarrhythmia based on the discrimination between monomorphic tachyarrhythmia and polymorphic tachyarrhythmia; and
selecting a therapy based on at least one of the discrimination between monomorphic tachyarrhythmia and polymorphic tachyarrhythmia and the classification of the arrhythmia episode type, wherein selecting the therapy includes selecting the therapy based on a history of success of the therapy at terminating the arrhythmia.

12. The method of claim 1, further comprising selecting a therapy to treat the arrhythmia episode based on a history of satisfactory treatment, wherein the history of satisfactory treatment is based on effectiveness of the selected therapy and at least one additional factor.

13. An implantable medical device, comprising:
sensor circuitry comprising electrodes for electrically coupling to a heart, the sensor circuitry configured to detect cardiac beats associated with an cardiac arrhythmia episode;
a template generator coupled to the sensor circuitry and configured to form a plurality of templates of the arrhythmia episode using the detected cardiac beats, wherein the template generator includes:
circuitry configured to form at least one template of the arrhythmia episode;
circuitry configured to measure a similarity between morphological features of a cardiac beat of the arrhythmia episode and each previously formed template of the arrhythmia episode;
circuitry configured to use the cardiac beat to modify a previously formed template of the arrhythmia episode in response to a measure of similarity between the cardiac beat and the previously formed template being greater than a similarity threshold; and
circuitry configured to form an additional template of the arrhythmia episode in response to measures of similarity between the cardiac beat and each previously formed template being less than a similarity threshold; and
an arrhythmia processor coupled to the template generator, the arrhythmia processor configured to determine the number of templates formed from the arrhythmia episode and discriminate between monomorphic tachyarrhythmia and polymorphic tachyarrhythmia based on the number of templates determined to be formed using the cardiac beats of the arrhythmia episode.

14. The device of claim 13, wherein the similarity of the one or more templates is determined by calculating a correlation coefficient comparing a template and a cardiac beat.

15. The device of claim 13, wherein the circuitry configured to form the plurality of templates further comprises circuitry configured to combine at least two previously formed templates of the plurality of templates and the cardiac beat to form an additional template and to erase the at least two previously formed templates in response to the similarity measure between the cardiac beat and the at least two previously formed templates being greater than a similarity threshold.

16. The device of claim 13, further comprising a memory for storing particular templates of the one or more templates, wherein the arrhythmia processor is configured to classify subsequently detected monomorphic arrhythmia episodes according to monomorphic arrhythmia type using the one or more of the particular templates.

17. The device of claim 16, further comprising:
a control system configured to select an electrical stimulation therapy to treat a subsequently detected monomorphic arrhythmia episode based on the classification according to monomorphic arrhythmia type; and
therapy circuitry configured to deliver the selected therapy.

18. The device of claim 13, further comprising:
a control system configured to select an electrical stimulation therapy based on the discrimination between monomorphic tachyarrhythmia and polymorphic tachyarrhythmia; and
therapy circuitry configured to deliver the selected therapy.

19. A system for arrhythmia discrimination, comprising:
means for detecting cardiac beats associated with an arrhythmia episode;
means for forming a plurality of templates of the arrhythmia episode using morphological features of the cardiac beats of the arrhythmia episode, wherein forming the plurality of templates includes:
means for forming at least one template of the arrhythmia episode;
means for measuring similarity between morphological features of a cardiac beat of the arrhythmia episode and each previously formed template of the arrhythmia episode;
means for using the cardiac beat to modify a previously formed template of the arrhythmia episode in response to a measure of similarity between the cardiac beat and the previously formed template being greater than a similarity threshold; and
means for forming an additional template of the arrhythmia episode in response to measures of similarity between the cardiac beat and each previously formed template being less than a similarity threshold;
means for determining the number of templates formed from the arrhythmia episode; and
means for discriminating between monomorphic tachyarrhythmia and polymorphic tachyarrhythmia based on the number of templates determined to be formed using the cardiac beats of the arrhythmia episode.

20. The system of claim 19, wherein the means for forming the plurality of templates further comprises means for forming an additional template of the arrhythmia episode in response to measures of similarity between the cardiac beat and at least two previously formed templates being greater than a similarity threshold.

21. The system of claim 19, further comprising means for classifying the arrhythmia episode according to monomorphic arrhythmia type if the arrhythmia episode is determined to be monomorphic tachyarrhythmia based on the discrimination between monomorphic tachyarrhythmia and polymorphic tachyarrhythmia.

22. The system of claim 21, further comprising means for selecting a therapy based on a history of satisfaction with the selected therapy, wherein the history of satisfaction is based on whether the therapy is effective and at least one additional factor.

* * * * *